(12) United States Patent
Norman et al.

(10) Patent No.: US 11,986,607 B2
(45) Date of Patent: May 21, 2024

(54) CATHETER STRUCTURE WITH IMPROVED SUPPORT AND RELATED SYSTEMS, METHODS, AND DEVICES

(71) Applicant: QXMedical, LLC, Roseville, MN (US)

(72) Inventors: William Norman, Columbia Heights, MN (US); Fernando Di Caprio, St. Paul, MN (US); Gianfranco Panarello, Mount Royal (CA)

(73) Assignee: QXMedical, LLC, Roseville, MN (US)

( * ) Notice: Subject to any disclaimer, the term of this patent is extended or adjusted under 35 U.S.C. 154(b) by 785 days.

(21) Appl. No.: 16/230,288

(22) Filed: Dec. 21, 2018

(65) Prior Publication Data

US 2019/0117938 A1 Apr. 25, 2019

Related U.S. Application Data

(63) Continuation-in-part of application No. 15/281,345, filed on Sep. 30, 2016, now Pat. No. 10,780,247.
(Continued)

(51) Int. Cl.
*A61M 25/01* (2006.01)
*A61M 25/00* (2006.01)
*A61M 25/06* (2006.01)

(52) U.S. Cl.
CPC .... *A61M 25/0147* (2013.01); *A61M 25/0045* (2013.01); *A61M 25/0052* (2013.01);
(Continued)

(58) Field of Classification Search
CPC .......... A61M 25/0147; A61M 25/0052; A61M 25/0662; A61M 25/0045; A61M 25/0054;
(Continued)

(56) References Cited

U.S. PATENT DOCUMENTS 4,543,089 A 9/1985 Moss
4,581,017 A 4/1986 Sahota
(Continued)

FOREIGN PATENT DOCUMENTS

EP 1457230 A1 9/2004
EP 2885017 A2 6/2015
(Continued)

OTHER PUBLICATIONS

International Patent Application No. PCT/US2016/054638, International Search Report and Written Opinion dated Dec. 28, 2016, 10 pages.

*Primary Examiner* — Lauren P Farrar
(74) *Attorney, Agent, or Firm* — Fredrikson & Byron, P.A.

(57) ABSTRACT

Certain embodiments herein relate to an extension catheter for positioning through a conventional guiding catheter into the vasculature of a patient, the extension catheter having a distal tubular member and a proximal elongated shaft coupled to the distal tubular member, wherein the proximal shaft has a length or section containing at least one discontinuous or segmented structure, and further wherein such structures that can be modified or varied to modify the torsional compliance characteristics of the device. Further embodiments relate to a multi-layer catheter having a protective wrap at or near the distal end of the catheter.

34 Claims, 18 Drawing Sheets

Related U.S. Application Data

(60) Provisional application No. 62/235,751, filed on Oct. 1, 2015.

(52) U.S. Cl.
CPC .... *A61M 25/0054* (2013.01); *A61M 25/0662* (2013.01); *A61M 2025/0004* (2013.01); *A61M 2025/0046* (2013.01); *A61M 2025/0047* (2013.01); *A61M 2025/0062* (2013.01); *A61M 25/0108* (2013.01); *A61M 2025/0175* (2013.01)

(58) Field of Classification Search
CPC .. A61M 2025/0175; A61M 2025/0004; A61M 2025/0062; A61M 2025/0047; A61M 25/0108
See application file for complete search history.

(56) References Cited

U.S. PATENT DOCUMENTS

| | | | |
|---|---|---|---|
| 4,867,174 A | 9/1989 | Skribiski | |
| 5,161,536 A | 11/1992 | Vilkomerson et al. | |
| 5,253,653 A | 10/1993 | Daigle et al. | |
| 5,256,144 A | 10/1993 | Kraus et al. | |
| 5,281,203 A | 1/1994 | Ressemann | |
| 5,290,247 A | 3/1994 | Crittenden | |
| 5,385,562 A | 1/1995 | Adams et al. | |
| 5,397,321 A | 3/1995 | Houser et al. | |
| 5,439,445 A | 8/1995 | Kontos | |
| 5,464,395 A | 11/1995 | Faxon et al. | |
| 5,466,222 A | 11/1995 | Ressemann et al. | |
| 5,591,194 A | 1/1997 | Berthiaume | |
| 5,620,417 A | 4/1997 | Jang et al. | |
| 5,718,678 A | 2/1998 | Fleming | |
| 5,779,671 A | 7/1998 | Ressemann et al. | |
| 5,782,811 A | 7/1998 | Samson et al. | |
| 5,830,181 A | 11/1998 | Thornton | |
| 5,833,644 A | 11/1998 | Zadno-Azizi et al. | |
| 5,911,715 A * | 6/1999 | Berg | A61M 25/0043 604/525 |
| 5,947,940 A | 9/1999 | Beisel | |
| 6,206,868 B1 | 3/2001 | Parodi | |
| 6,248,100 B1 | 6/2001 | De Toledo et al. | |
| 6,283,940 B1 | 9/2001 | Mulholland | |
| 8,048,032 B2 | 11/2011 | Root et al. | |
| 8,142,413 B2 | 3/2012 | Root et al. | |
| 8,292,850 B2 | 10/2012 | Root et al. | |
| 8,947,940 B2 | 2/2015 | Mu et al. | |
| 2001/0039411 A1 | 11/2001 | Johansson et al. | |
| 2003/0050600 A1 | 3/2003 | Ressemann et al. | |
| 2004/0236215 A1 * | 11/2004 | Mihara | A61M 25/0102 604/528 |
| 2005/0004553 A1 | 1/2005 | Douk | |
| 2005/0165383 A1 | 7/2005 | Eshel et al. | |
| 2007/0016133 A1 | 1/2007 | Pepper | |
| 2007/0112302 A1 | 5/2007 | Yu | |
| 2008/0287786 A1 | 11/2008 | Lentz | |
| 2010/0114062 A1 | 5/2010 | Wilson et al. | |
| 2010/0217237 A1 | 8/2010 | Itou et al. | |
| 2011/0021847 A1 | 1/2011 | Forestiere et al. | |
| 2011/0071497 A1 * | 3/2011 | Alinsod | A61M 25/0014 604/509 |
| 2011/0251519 A1 | 10/2011 | Romoscanu | |
| 2012/0296366 A1 * | 11/2012 | Rundquist | A61M 25/005 219/121.64 |
| 2012/0302953 A1 | 11/2012 | Don Michael | |
| 2013/0116701 A1 | 5/2013 | Wang et al. | |
| 2013/0197483 A1 * | 8/2013 | Anderson | A61M 25/0105 604/528 |
| 2013/0237962 A1 | 9/2013 | Kawai | |
| 2014/0081243 A1 | 3/2014 | Zhou et al. | |
| 2014/0276618 A1 * | 9/2014 | Di Caprio | A61M 25/0068 604/510 |

FOREIGN PATENT DOCUMENTS

| | | |
|---|---|---|
| JP | H10-263088 A | 10/1998 |
| JP | H11-319074 A | 11/1999 |
| JP | 2004275435 A | 10/2004 |
| JP | 2007517586 A | 7/2007 |
| JP | 2012223207 A | 11/2012 |
| WO | 9403230 A1 | 2/1994 |
| WO | 2006010929 | 2/2006 |
| WO | 2011019359 A1 | 2/2011 |
| WO | 2011086758 A1 | 7/2011 |
| WO | 2011154128 A1 | 12/2011 |

* cited by examiner

CATHETER STRUCTURE WITH IMPROVED SUPPORT AND RELATED SYSTEMS, METHODS, AND DEVICES

CROSS-REFERENCE TO RELATED APPLICATION

This application claims priority as a continuation-in-part application to U.S. application Ser. No. 15/281,345, filed Sep. 30, 2016 and entitled "Catheter Structure with Improved Support and Related Systems, Methods, and Devices" which claims the benefit under 35 U.S.C. § 119(e) to U.S. Provisional Application 62/235,751, filed Oct. 1, 2015 and entitled "Catheter Structure with Improved Support and Related Systems, Methods, and Devices," both of which are hereby incorporated herein by reference in their entireties.

FIELD OF THE INVENTION

The various embodiments disclosed herein relate to catheters for use as medical devices, including extension catheters (as defined herein) for use with guiding catheter systems, and more particularly to catheters having a length or section containing a discontinuous or segmented structure, including such structures that can be modified or varied to modify the torsional compliance characteristics of the device. Further embodiments relate to an improved catheter tip for incorporation into the various types of catheters, especially those having multi-layer tubes.

BACKGROUND OF THE INVENTION

The general use of catheters as medical devices is fairly well-developed at this point. U.S. Pat. No. 4,581,017 to Sahota, for example, shows the use of a guide catheter for insertion into an artery to assist with treating the artery (e.g. with a stenosis); and it further shows the use of another catheter for telescoping insertion into the first catheter to extend beyond the first catheter to treat or access portions of the artery that the first catheter cannot reach because of its larger diameter or lack of flexibility, trackability or support. Subsequent patents show further developments of such telescoping or extension catheter systems. For example, U.S. Pat. No. 5,385,562 to Adams et al., U.S. Pat. No. 5,439,445 to Kontos, and U.S. Pat. No. 5,290,247 to Crittendon all show the use of a catheter having a tubular portion that extends or telescopes beyond the guiding catheter, and an elongated manipulation/insertion wire or shaft attached to the tubular portion to manipulate the tubular portion axially—in push/pull fashion—within the guiding catheter after it has been inserted through the hemostasis valve and into the guiding catheter. The Adams '562 patent suggests that the proximal manipulation/insertion wire may actually be a low-diameter tubular shaft for conducting fluid to inflate and deflate a restriction balloon that restricts movement of the tubular portion.

Certain known extension catheters have proximal shafts that transfer twisting motion (also referred to as "torque") by the user from the proximal shaft to the distal tube. In addition, torsion is also generated along the proximal shaft of such devices as a result of urging the catheter distally or proximally through the guiding catheter and further through tortuous vasculature. However, this transmission of torque can induce stresses on the connection between the proximal shaft and the tube, in some cases stresses that are so great that the stresses cause failure or separation of the shaft and tube at the connection point. Thus, the torque generated at the connection point as a result of the low torsional compliance characteristics (including, for example, high torque transmission) of these devices coupled with the tensile or compressive forces generated from urging the catheter axially can cause device failures. Many of these known catheters have proximal shafts with low torsional compliance, thus making them susceptible to the problems described above.

Further, many of the catheters discussed above are multi-layer catheters. A multi-layer catheter is a catheter having a multi-layer tubular construction. Many known catheters can have such a multi-layer tubular construction, including guiding catheters, sheaths, guide extension catheters, and boosting catheters, for example. Typically, the multi-layer catheters have at least two layers: an inner liner layer and an outer layer. In many cases, the inner liner layer is a lubricious liner that is intended to facilitate the passage of other devices through the inner lumen of the catheter. Such an inner layer is often made of PTFE, but can also be made of Teflon, polyethylene, or any other known material that can be incorporated into a medical device.

One disadvantage of a multi-layer catheter is the possible delamination that can occur between layers. That is, one or more layers of the multi-layer catheter tube begin to separate from the rest of the layers. This is especially common with lubricious layers. For example, the distal end 322 of a typical known multi-layer tubular catheter 320 with exposed ends of the layers is shown in FIG. 14A. Note that the catheter has an inner layer 324 and an outer layer 326, and both layers are exposed at the distal end 322 of the catheter 320. As shown in FIG. 14B, one common problem with multi-layer catheters is delamination of the inner layer 324 from the adjacent layer (in this case, the outer layer 326), such as at the distal end 322 as shown. According to one exemplary scenario, the delamination can occur during use of the catheter 320 when the tube is being flexed or advanced through the vasculature. A result of such a delamination is that passage (especially withdrawal) of a device through the distal tip may be impaired.

Another disadvantage of a catheter having a proximal shaft coupled to a distal tube is that the typically metallic proximal or manipulation shaft may shear, delaminate, peel or disconnect from the distal tube during use.

Accordingly, there has been a need in the art for improved catheters and/or improved catheter tips and related methods and systems.

SUMMARY OF THE INVENTION

Discussed herein are various catheter embodiments for use with standard guiding catheters and sheaths.

In Example 1, a catheter comprises a distal tube comprising a tubular wall and a tube lumen defined within the tube by the tubular wall, a support membrane disposed around a portion of the distal tube, and a proximal shaft operably coupled to a proximal portion of the distal tube. The proximal shaft comprises first and second elongate members and a first sheath segment disposed around a first length of the first and second elongate members such that the first length of the first and second elongate members is disposed within the first sheath segment. The first and second elongate members are configured to extend distally into a portion of the distal tube.

Example 2 relates to the catheter according to Example 1, wherein the proximal shaft further comprises a second sheath segment disposed around a second length of the first and second elongate members such that the second length of the first and second elongate members is disposed within the second sheath segment, wherein a total length of the first and second sheath segments is less than a total length of the first and second elongate members.

Example 3 relates to the catheter according to Example 1, wherein the proximal shaft further comprises a second sheath segment disposed around a second length of the first and second elongate members such that the second length of the first and second elongate members is disposed within the second sheath segment; and at least one unsheathed segment wherein a length of the first and second elongate members is not disposed within the sheath.

Example 4 relates to the catheter according to Example 1, wherein the proximal shaft comprises at least one additional sheath segment, wherein each of the at least one additional sheath segments is disposed around a different length of the first and second elongate members.

Example 5 relates to the catheter according to Example 4, wherein the proximal shaft comprises at least one unsheathed segment wherein a length of the first and second elongate members is not disposed within the sheath.

Example 6 relates to the catheter according to Example 1, wherein at least one of the first and second elongate members defines a lumen within the at least one of the first and second elongate members.

Example 7 relates to the catheter according to Example 1, wherein at least one of the first and second elongate members has no lumen.

Example 8 relates to the catheter according to Example 1, wherein the first elongate member is configured to extend distally into a first portion of the tubular wall, and further wherein the second elongate member is configured to extend distally into a second portion of the tubular wall.

Example 9 relates to the catheter according to Example 1, wherein the proximal shaft further comprises a shaft lumen defined by the first sheath segment.

Example 10 relates to the catheter according to Example 9, wherein the proximal shaft further comprises a distal opening in fluid communication with the shaft lumen, whereby the shaft lumen is in fluid communication with the tube lumen.

Example 11 relates to the catheter according to Example 10, wherein the shaft lumen is configured to receive fluid such that fluid can be caused to flow distally through the proximal shaft and out of the distal opening.

Example 12 relates to the catheter according to Example 10, wherein the proximal shaft is configured to extend distally into a portion of the tubular wall such that the shaft lumen extends distally into the tubular wall and such that the distal opening is in fluid communication with the tube lumen.

Example 13 relates to the catheter according to Example 9, wherein the shaft lumen is not in fluid communication with the tube lumen.

Example 14 relates to the catheter according to Example 9, wherein the proximal shaft further comprises a distal opening in fluid communication with the shaft lumen, whereby the shaft lumen is in fluid communication with an area external to the catheter.

Example 15 relates to the catheter according to Example 9, wherein the proximal shaft further comprises a distal opening in fluid communication with the shaft lumen, whereby the shaft lumen is in fluid communication with an area external to the catheter and proximal to the distal tube.

Example 16 relates to the catheter according to Example 9, wherein the proximal shaft further comprises a distal opening in fluid communication with the shaft lumen, whereby the shaft lumen is in fluid communication with an area external to the catheter and distal to the distal tube.

Example 17 relates to the catheter according to Example 1, further comprising at least one support member disposed in the proximal portion of the distal tube.

Example 18 relates to the catheter according to Example 1, wherein a distal portion of the proximal shaft is at least one support member disposed in the proximal portion of the distal tube.

Example 19 relates to the catheter according to Example 1, wherein the proximal shaft comprises a third elongate member.

Example 20 relates to the catheter according to Example 19, wherein the proximal shaft comprises at lease one additional elongate member.

Example 21 relates to the catheter according to Example 1, further comprising a filler material disposed within at least a portion of the first sheath segment.

Example 22 relates to the catheter according to Example 1, further comprising a filler material disposed within at least a portion of the first sheath segment and at least a portion of a second sheath segment.

Example 23 relates to the catheter according to Example 1, wherein the first length of the first and second elongate members is an entire length of the first and second elongate members, such that the first sheath segment is disposed around the entire length of the first and second elongate members.

Example 24 relates to the catheter according to Example 1, wherein the first length of the first and second elongate members is a portion of an entire length of the first and second elongate members such that the first sheath segment is disposed around the portion of the entire length of the first and second elongate members.

Example 25 relates to the catheter according to Example 1, further comprising a second sheath segment disposed around a second length of the first and second elongate members such that the second length of the first and second elongate members is disposed within the second sheath segment, wherein the proximal shaft further comprises a first shaft lumen defined by the first sheath segment and a second shaft lumen defined by the second sheath segment.

In Example 26, a catheter comprises a distal tube comprising a tubular wall and a tube lumen defined within the tube by the tubular wall, a support membrane disposed around a portion of the distal tube, and a proximal shaft operably coupled to a proximal portion of the distal tube. The proximal shaft comprises first and second elongate members, at least one sheath segment disposed around a length of the first and second elongate members such that the length of the first and second elongate members is disposed within the at least one sheath segment, and at least one unsheathed segment wherein a length of the first and second elongate members is not disposed within any sheath segment. The first and second elongate members are configured to extend distally into a portion of the distal tube.

Example 27 relates to the catheter according to Example 26, wherein characteristics of the at least one sheath segment determine torsional compliance characteristics of the catheter.

Example 28 relates to the catheter according to Example 26, wherein the first and second elongate members are disposed in rolling contact with each other along the unsheathed segment.

Example 29 relates to the catheter according to Example 26, wherein the first and second elongate members are disposed in sliding contact with each other along the unsheathed segment.

Example 30 relates to the catheter according to Example 26, wherein the first and second elongate members are disposed in rolling and sliding contact with each other along the unsheathed segment.

Example 31 relates to the catheter according to Example 26, wherein the first and second elongate members are disposed in rolling contact with each other within the sheath segment.

Example 32 relates to the catheter according to Example 26, wherein the first and second elongate members are disposed in sliding contact with each other within the sheath segment.

Example 33 relates to the catheter according to Example 26, wherein the first and second elongate members are disposed in rolling and sliding contact with each other within the sheath segment.

Example 34 relates to the catheter according to Example 26, wherein characteristics of the at least one unsheathed segment determine torsional compliance characteristics of the catheter.

In Example 35, a method of using an extension catheter in combination with a standard guiding catheter to perform a procedure at a predetermined location within the vasculature of a patient comprises positioning the standard guiding catheter into a target vessel in the patient, selecting the extension catheter based on desired torsional compliance characteristics, inserting the extension catheter into the standard guiding catheter, urging the extension catheter distally through the standard guiding catheter such that a distal portion of the distal tube extends distally out of the distal end of the standard guiding cathether, and performing a procedure through the extension catheter and standard guiding catheter. The extension catheter comprises a distal tube comprising a tubular wall and a tube lumen defined within the tube by the tubular wall, a support membrane disposed around a portion of the distal tube, and a proximal shaft operably coupled to a proximal portion of the distal tube. The proximal shaft comprises first and second elongate members, at least one sheath segment disposed around a length of the first and second elongate members such that the length of the first and second elongate members is disposed within the at least one sheath segment, and at least one unsheathed segment wherein a length of the first and second elongate members is not disposed within any sheath segment. The torsional compliance characteristics are determined based on the at least one sheath segment and the at least one unsheathed segment.

Example 36 relates to the method according to Example 35, wherein an increase in size or number of the at least one sheath segment decreases the torsional compliance characteristics of the catheter.

Example 37 relates to the method according to Example 35, wherein an increase in size or number of the at least one unsheathed segment increases the torsional compliance characteristics of the catheter.

Example 38 relates to the method according to Example 35, further comprising adding a filler material to at least a portion of the sheath segment, wherein the filler material is a binding material, wherein adding the binding material decreases the torsional compliance characteristics of the catheter.

Example 39 relates to the method according to Example 35, further comprising adding a filler material to at least a portion of the sheath segment, wherein the filler material is a lubricant, wherein adding the lubricant increases the torsional compliance characteristics of the catheter.

Example 40 relates to the catheter according to Example 1, wherein the support membrane is a partial circumference membrane.

Example 41 relates to the catheter according to Example 1, wherein the distal tube further comprises a protective wrap disposed around a portion of a proximal opening of the distal tube.

Example 42 relates to the catheter according to Example 1, wherein the distal tube comprises a distal portion that has a higher stiffness than a proximal portion.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The various embodiments disclosed and contemplated herein relate to a catheter, such as an extension guide catheter, having a length or section containing a discontinuous or segmented structure. Further embodiments relate to catheters having such discontinuous or segmented structures that can be modified or varied to modify the torsional compliance characteristics of the device. Certain of these catheter embodiments can be adapted to be positioned through and extend distally from a conventional guiding catheter or sheath, wherein the guiding catheter or sheath is adapted to extend into a patient.

Further embodiments disclosed and contemplated herein relate to an improved catheter tip that can be incorporated into any known multi-layer catheter, including an extension catheter, guiding catheter, sheath, delivery catheter, or any other such catheter.

Additional embodiments disclosed and contemplated herein relate to a support layer than can be positioned around a portion of any known catheter to provide additional strength and/or support to the catheter.

Further implementations disclosed and contemplated herein relate to an improved proximal portion of a catheter tube that can be incorporated into any known multi-layer catheter, including an extension catheter, guiding catheter, sheath, delivery catheter, or any other such catheter.

For purposes of the remainder of this application, it is understood that the term "guiding catheter" relates to any known guiding catheter, sheath, or delivery system. Additionally, for purposes of this application, "extension catheter" and "extension guide catheter" shall mean any catheter that can be used in combination with a guiding catheter to perform a procedure, including a boosting catheter. It is understood that the various embodiments disclosed herein can be incorporated into any extension catheter, but also can be incorporated into other types of catheters as well.

Figure 1:
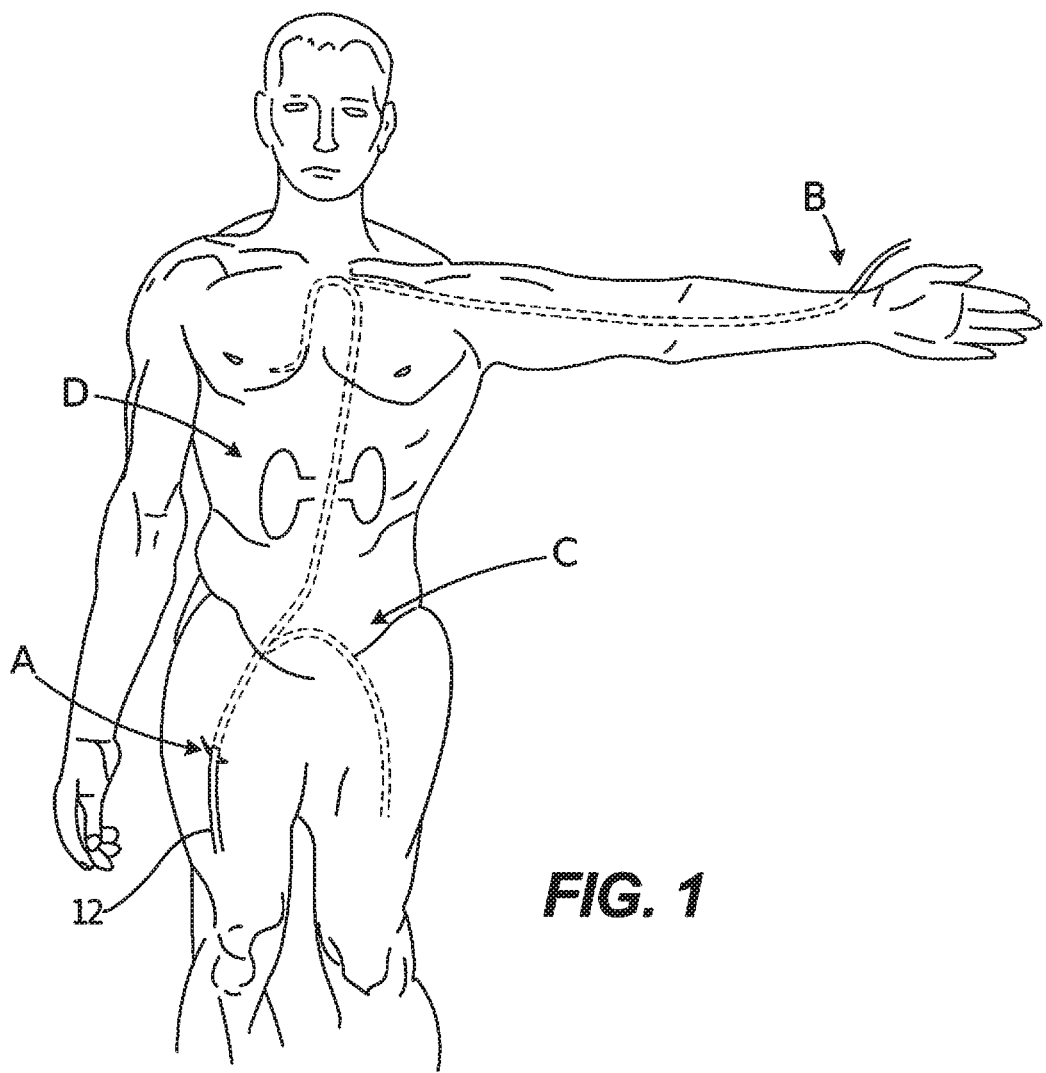
FIG. 1 is an environmental view showing the use of one embodiment of the subject device in a conventional guiding catheter, which is used to perform various medical procedures.

FIG. 1 depicts a conventional guiding catheter 12 being used in the general operating environment, which is partially within a human body, and usually within an artery or vein. As shown in the figure, the guiding catheter 12 may be inserted into the vasculature through a number of different access points in the body. For example, a femoral artery approach is shown at A, while a radial artery approach is shown at B. Further, other parts of the vasculature may be accessed with various guiding catheters or sheaths. For example, at C, a sheath is shown inserted through the femoral artery for a contralateral approach for procedures in the leg or other parts of the body. In another example, the sheath is inserted through the femoral artery to access the renal arteries in one of the kidneys at D or to access the coronary vasculature.

Regardless of the access point or the target portion of the vasculature, certain catheter implementations disclosed herein are extension catheter embodiments that can be used in combination with guiding catheters to assist with various procedures. For example, the extension catheter embodiments in combination with guiding catheters can be used to assist with the passage of other interventional, diagnostic, or therapeutic devices to various locations in the vasculature. In other instances, the various types of catheters can be used in combination with guiding catheters or sheaths to assist with the transmission of contrast, diagnostic, or therapeutic fluids/agents by injecting the fluids/agents through the catheter to various locations, or by transmitting the fluids/agents through the guiding catheter via a hemostasis valve adaptor and subsequently passing it through the distal tube of the catheter. In another example, the various catheter types in combination with guiding catheters or sheaths can be used to assist with the removal of thrombus, emboli, or debris present in the vasculature through the guiding catheter/sheath by applying a vacuum at the proximal end of the guiding catheter/sheath via a hemostasis valve adaptor. Alternatively, other catheter implementations are contemplated.

Figure 2A:
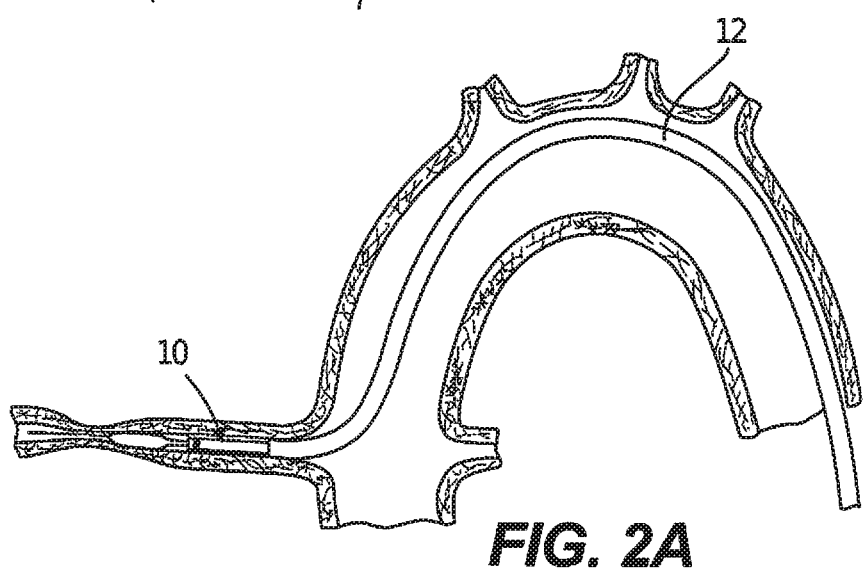
FIG. 2A is a closer environmental view showing the distal end of an extension catheter extending out the end of a conventional guiding catheter engaged in the coronary vasculature, according to one embodiment.
Figure 2B:
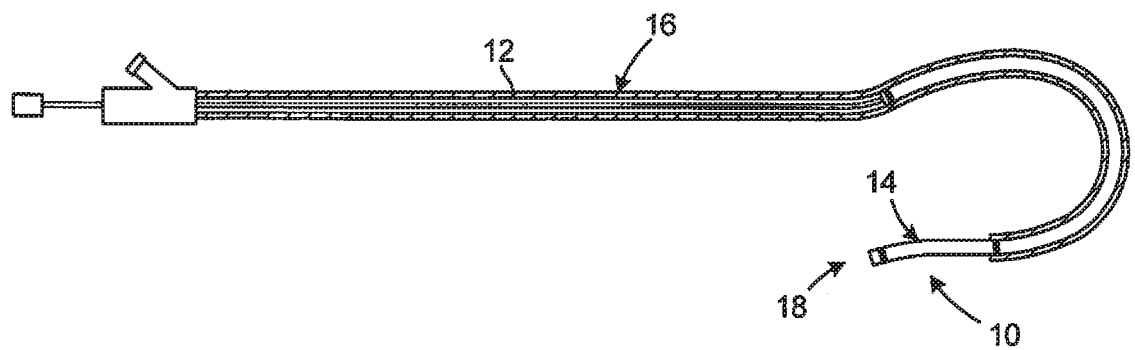
FIG. 2B is another environmental view showing an extension catheter in a guiding catheter and including a proximal portion and a distal portion, according to one embodiment.

As shown in FIGS. 2A and 2B, various embodiments of an extension catheter (generally shown at 10) as disclosed and contemplated herein can be used in conjunction with any conventional guiding catheter 12 for purposes of the various procedures described above. Generally, the distal end of the extension catheter 10 is positioned through and extended distally from the distal end of the conventional guiding catheter 12. As best shown in FIG. 2B, the various catheter embodiments, including catheter 10 as shown, have two basic parts: a distal portion that is a comparatively large diameter tube (generally indicated at 14) defining a lumen 18 and adapted to extend through and beyond the distal end of the guiding catheter; and a proximal portion that is a comparatively smaller diameter elongate member, also referred to herein as a "manipulation shaft" (generally indicated at 16), connected to the tubular portion 14 at a junction.

In the various implementations disclosed or contemplated herein, the proximal elongated shaft 16 is made up of at least two rods. In certain embodiments, the proximal shaft also has a sheath disposed around the at least two rods, such that the two rods are disposed within or through the sheath. The sheath is any structure that forms a lumen that is configured to receive the two or more rods of the proximal shaft (such as shaft 16) as disclosed or contemplated herein, and can also be referred to herein as a "tube." In further embodiments, the sheath is discontinuous. That is, in those embodiments, at least one length of the two rods is not disposed within the sheath. In other implementations, the sheath can cover the entire length of the at least two rods.

In addition to serving as a mechanism for advancing the catheter in certain implementations, a manipulation shaft with at least two rods within a discontinuous sheath can have desirable torsional compliance characteristics, as will be explained in detail below. The torsional compliance characteristics of these embodiments can help to reduce incidence of stress at the joint or connection between the manipulation shaft and distal tube, thereby reducing the incidence of failure of that joint.

Figure 3A:
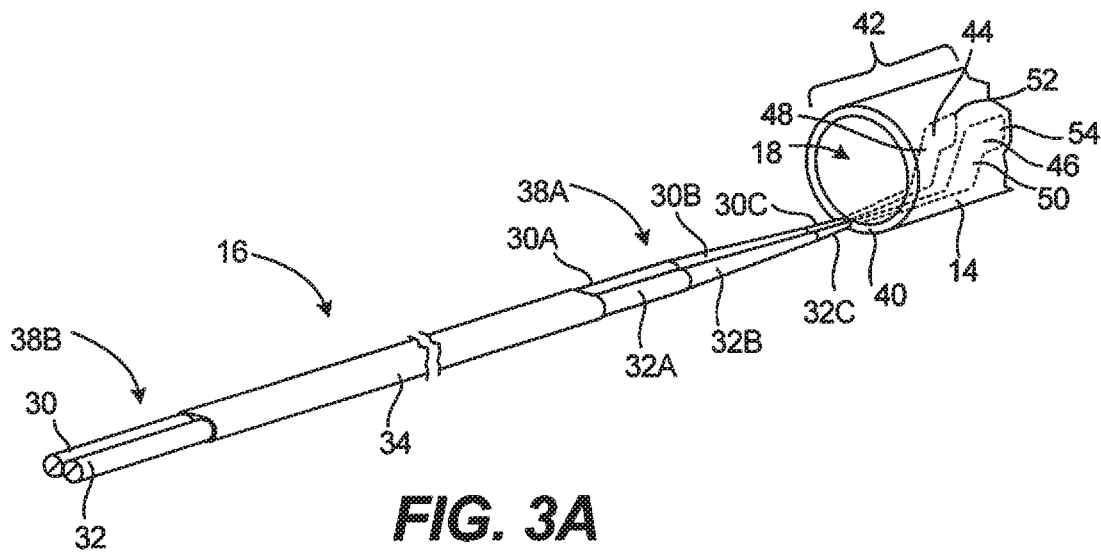
FIG. 3A is a perspective view of an extension catheter having a manipulation shaft with two elongate members, according to one embodiment.
Figure 3B:
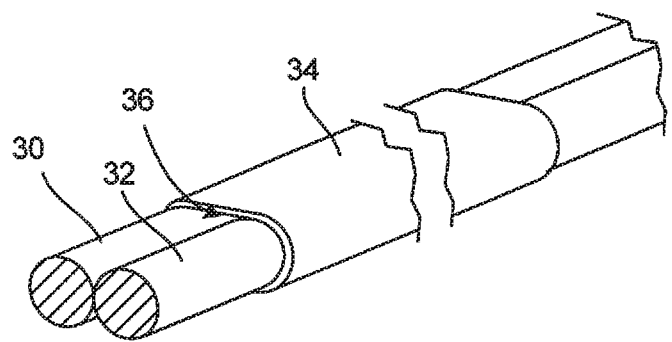
FIG. 3B is a close-up perspective view of the manipulation shaft of the extension catheter of FIG. 3A.
Figure 3C:
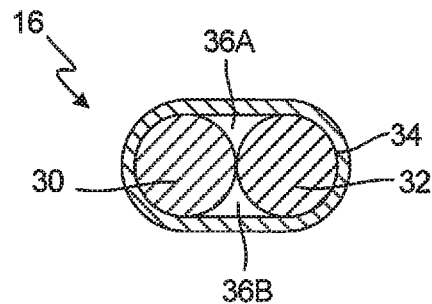
FIG. 3C is an end view of the manipulation shaft of FIG. 3A.

One example of an extension catheter embodiment 10 with a manipulation shaft 16 made up of two elongate members 30, 32 and a sheath segment 34 is shown in further detail in FIGS. 3A-3C. The elongate members 30, 32 can be rods, tubes, or any other type of elongate member that can be used to advance a catheter or other similar medical device. The two elongate members 30, 32 in this embodiment are rods 30, 32 that do not contain lumens and are positioned generally adjacent to each other. The sheath segment 34 is positioned around the two rods 30, 32 such that the two rods 30, 32 are positioned through the lumen 36 formed in the segment 34. In this implementation, the sheath segment 34 has a length that is shorter than the length of the two rods 30, 32 such that the entire length of the rods 30, 32 is not covered by the sheath segment 34. That is, in this embodiment, the rods 30, 32 have an uncovered (or "unsheathed") distal portion 38A and an unsheathed proximal portion 38B, with the sheath segment 34 positioned between the two unsheathed segments 38A, 38B.

In this implementation, each of the rods 30, 32 has a full diameter portion 30A, 32A and a reduced diameter portion 30C, 32C, with a transition portion 30B, 32B therebetween. As shown, the transition portions 30B, 32B in this embodiment are tapered portion 30B, 32B. In accordance with one implementation, the reduced diameter portions 30C, 32C can provide enhanced flexibility and are sized such that the diameter of the rods 30, 32 at their reduced diameter portions 30C, 32C can be positioned within the wall 40 of the distal tube 14 as described below.

In this implementation, the manipulation shaft 16 is coupled to the distal tube 14 at a point or area of the wall 40 of the tube 14. More specifically, as best shown in FIG. 3A, a distal portion of the shaft 16 is coupled to and integral with the wall 40 of the distal tube 14 at a connection zone 42. The connection zone (also referred to as the "coupling zone" or "transition zone") 42 is the portion or length of the proximal end of the distal tube 14 in which a length of the manipulation shaft 16 is coupled or otherwise positioned. In this specific embodiment, as best shown in FIG. 3A, the two rods 30, 32 extend into the distal tube 14. More specifically, the distal portion 44 of rod 30 is disposed in one portion of the wall 40 in the connection zone 42 of the distal tube 14 while the distal portion 46 of rod 32 is disposed in another portion of the wall 40, as will be described in further detail below.

Further, in this implementation as best shown in FIG. 3A, both distal portions 44, 46 are positioned in the connection zone 42 in a specific configuration. More specifically, each of the distal portions 44, 46 has an angled portion 48, 50 that extends at an angle in relation to the longitudinal axis of the tube 14 and an axial portion 52, 54 that extends axially for some distance as well, as shown. As shown, in this configuration, the proximal ends of the distal portions 44, 46 in the connection zone 42 are substantially adjacent to each other in the wall 40. In contrast, the angled portions 48, 50 of the distal portions 44, 46 are farther apart from each other. That is, the distal portions 44, 46 of the rods 30, 32 are positioned such that they are farther apart from each other at the distal ends of the distal portions 44, 46 in comparison to the proximal ends. Thus, in accordance with one implementation, the axial portions 52, 54 of the distal portions 44, 46 are positioned in the wall 40 contralaterally in relation to each other. That is, the axial portion 52 of rod 30 is disposed in the wall 40 on one side of the tube 14 while the axial portion 54 is disposed in the wall 40 on the other side of the tube 14 such that the portions 52, 54 are positioned across the lumen 18 from each other.

Further, according to certain embodiments, the distal portions 44, 46 positioned in the connection zone are configured to be substantially flat or have a reduced cross-sectional profile that allows the distal portions 44, 46 to be positioned within the wall 40 of the tube 14 as described herein. Alternatively, other configurations are also contemplated.

Figure 4A:
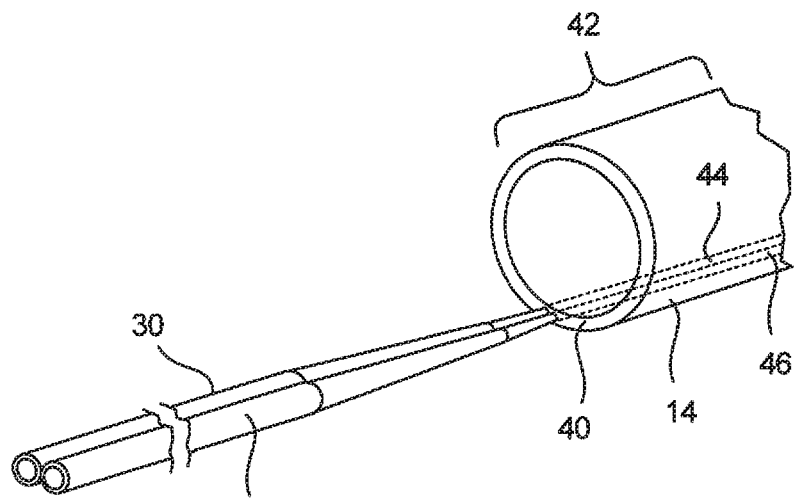
FIG. 4A is a perspective view of an extension catheter, according to another embodiment.
Figure 4B:
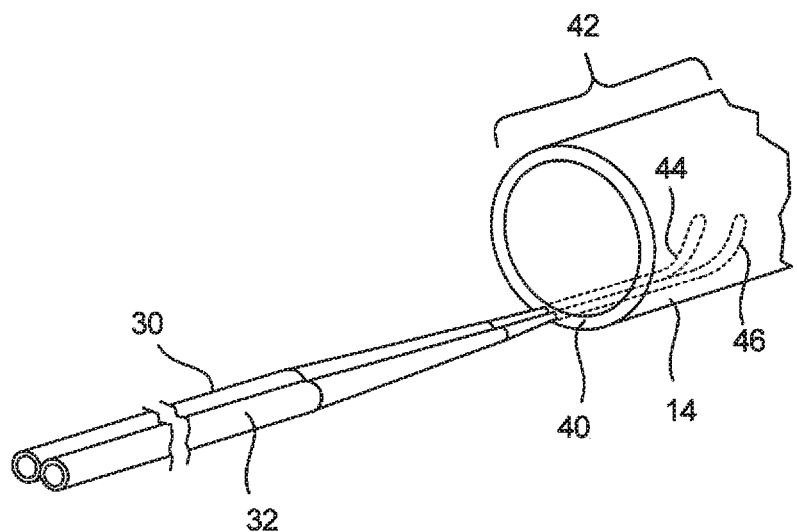
FIG. 4B is a perspective view of another extension catheter, according to a further embodiment.

For example, FIGS. 4A and 4B depict alternative embodiments of the distal portions 44, 46 of rods 30, 32. It should be noted that while these two embodiments are depicted without any sheaths or sheath segments, it is understood that either or both can have one or more sheath segments or a single sheath that extends along the entire length of the rods 30, 32 or any portion thereof. In FIG. 4A, the distal portions 44, 46 in the connection zone 42 are straight. That is, there are no angled or curved portions. Alternatively, in FIG. 4B, the distal portions 44, 46 have a gradual curve configuration. As shown, the rods 30, 32 in FIGS. 4A and 4B are round. Alternatively, the distal portions 44, 46 can be flattened or have a reduced cross-sectional profile. Further, in certain implementations, the distal portions 44, 46 can have geometrical features (such as barbs, notches, holes, etc.) that may enhance the retention of the rods 30, 32 within the tube. In further alternatives, the distal portions 44, 46 can have multiple curves or bends and can either be round or flattened.

In accordance with one implementation, the positioning and configuration of the distal portions 44, 46 of the rods 30, 32 in the connection zone 42 in the wall 40 of the distal tube 14, according to any of the embodiments depicted in FIGS. 3A-4B, can enhance the kink resistance of that portion of the tube 14 as well as assisting in transmitting a distal or proximal force to the distal tube 14 in a more even fashion during use of the catheter 10. Further, in a similar fashion to the geometrical features discussed above, the configuration of the distal portions 44, 46 can also enhance the retention strength of the connection between the manipulation shaft 16 and the distal tube 14 by increasing the surface area of the connection and thereby further distributing the stresses placed upon the connection when forces are applied to the manipulation shaft 16 (or the distal tube 16).

As discussed above, the rods 30, 32 in the embodiments depicted in FIGS. 3A-3C and 4B are solid rods (that is, they do not have lumens therein). In another embodiment as shown in FIG. 4A, the rods 30, 32 are tubes 30, 32, with each of the tubes 30, 32 having lumens defined therein. Further, in the embodiment of FIGS. 3A-3C as best shown in FIG. 3C, the two rods 30, 32 are disposed within the sheath 34 such that the sheath segment 34 has a lumen 36. More specifically, this particular configuration of the sheath 34 with two rods 30, 32 positioned adjacent to each other within the sheath 34 has two lumens 36A, 36B.

Figure 5A:
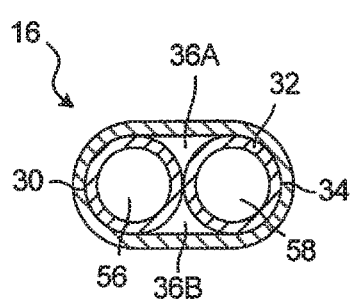
FIG. 5A is a cross-sectional view of a proximal shaft of an extension catheter, according to one implementation.
Figure 5B:
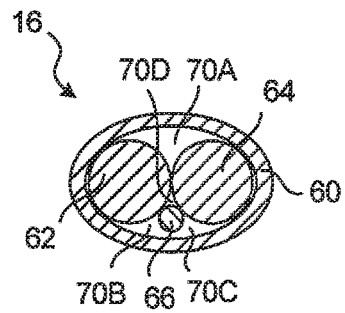
FIG. 5B is a cross-sectional view of a proximal shaft of an extension catheter, according to another implementation.
Figure 5C:
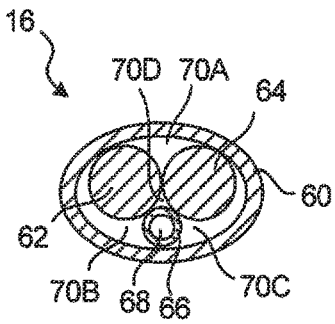
FIG. 5C is a cross-sectional view of a proximal shaft of an extension catheter, according to a further implementation.
Figure 5D:
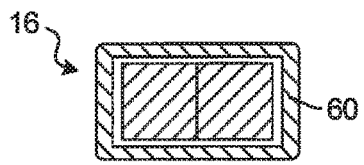
FIG. 5D is a cross-sectional view of a proximal shaft of an extension catheter, according to yet another implementation.
Figure 5E:
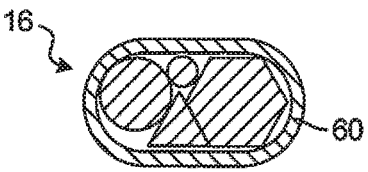
FIG. 5E is a cross-sectional view of a proximal shaft of an extension catheter, according to another embodiment.
Figure 5F:
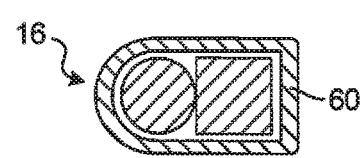
FIG. 5F is a cross-sectional view of a proximal shaft of an extension catheter, according to a further embodiment.
Figure 5G:
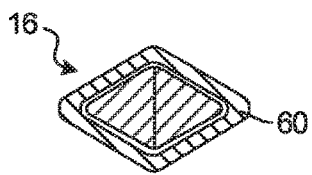
FIG. 5G is a cross-sectional view of a proximal shaft of an extension catheter, according to yet another embodiment.
Figure 5H:
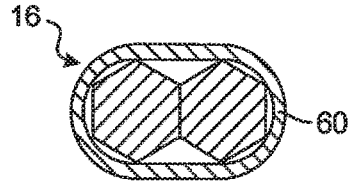
FIG. 5H is a cross-sectional view of a proximal shaft of an extension catheter, according to another implementation.
Figure 5I:
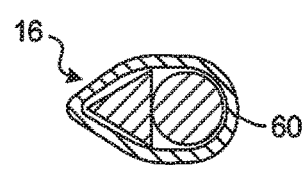
FIG. 5I is a cross-sectional view of a proximal shaft of an extension catheter, according to a further implementation.
Figure 5J:
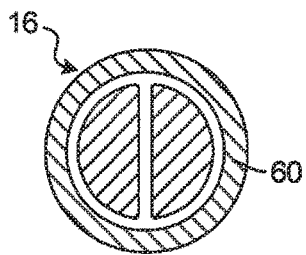
FIG. 5J is a cross-sectional view of a proximal shaft of an extension catheter, according to another implementation.
Figure 5K:
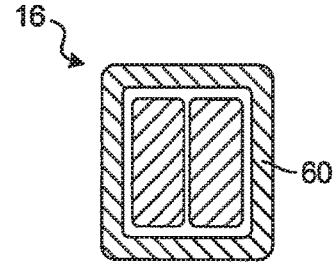
FIG. 5K is a cross-sectional view of a proximal shaft of an extension catheter, according to a further implementation.
Figure 5L:
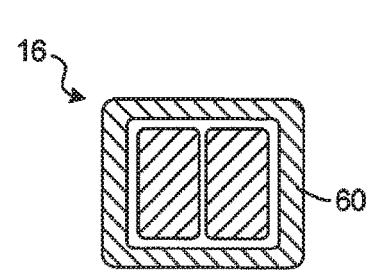
FIG. 5L is a cross-sectional view of a proximal shaft of an extension catheter, according to another implementation.
Figure 5M:
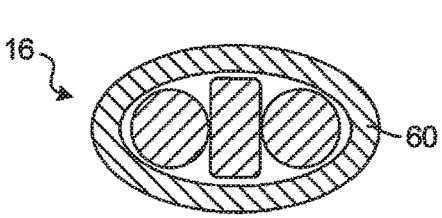
FIG. 5M is a cross-sectional view of a proximal shaft of an extension catheter, according to a further implementation.
Figure 5N:
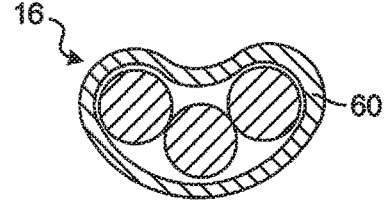
FIG. 5N is a cross-sectional view of a proximal shaft of an extension catheter, according to another implementation.

In alternative implementations, other configurations of the manipulation shaft 16 are possible, as shown in FIGS. 5A-5N. For example, as shown in FIG. 5A, the two rods 30, 32 can have lumens 56, 58 defined therein (rather than being solid rods). In this implementation, the rods 30, 32 can be hypotubes 30, 32, with each having a lumen 56, 58 defined therein. In addition, like the solid rods 30, 32 depicted in FIG. 3C, the sheath segment 34 also has two lumens 36A, 36B defined between the rods 30, 32 and the sheath 34. Further, it is understood that any of the sheath segment embodiments disclosed or contemplated herein with two or more elongate members may also have lumens in the spaces created by the elongate members disposed therein.

Further, FIGS. 5B-5N show that the shaft 16 can, in certain embodiments, have various configurations relating to the number, shape, and size of the elongate members. For example, in the implementation of FIG. 5B, the shaft 16 has a sheath segment 60 with two large rods 62, 64 and one small rod 66. Further, the sheath 60 also has lumens 70A, 70B, 70C, 70D defined within the sheath 60 as a result of the configuration of the rods 62, 64, 66. Each elongate member 62, 64, 66 disposed within the sheath 60 provides additional support or reinforcement to the shaft 16 while also resulting in multiple lumens within the segment 60. Alternatively, as shown in FIG. 5C, the shaft 16 can have the same configuration, except that the small rod 66 is a tube 66 having a lumen 68. Additional configurations are shown in FIGS. 5D-5N, including configurations with rods that are not round, but instead are square, rectangular, triangular, hexagonal, or other shapes or combinations thereof. Alternatively, any of the rods can be any known shape. As shown in these figures, the configuration, shape, and number of rods can also influence the cross-sectional shape or profile and the torsional characteristics of the segment 60.

In the various implementations disclosed or contemplated herein, the one or more lumens defined within the sheath segments (such as lumens 36A, 36B and lumens 70A, 70B, 70C, 70D described above) extend along the entire length of the sheath segment (such as segment 34 and segment 60).

According to certain embodiments, a filler material such as an adhesive, binding material, or polymer can be injected or otherwise positioned within one or more of the lumens (such as lumens 36A, 36B, or 70A, 70B, 70C, 70D) and serve as a bonding agent. The filler material can provide additional structural support for the shaft 16. Alternatively, the filler material can be a lubricant. The filler material can fill an entire lumen of a sheath segment (such as one or more of the lumens 36A, 36B or lumens 70A, 70B, 70C, 70D), the entire length of all of the lumens of a segment and/or all the segments, a portion of each of the lumens of each segment, only a portion of the length of any segment, or two or more portions of the length of any segment or all segments. Further, it is understood that the filler material can fill one sheath segment (such as one sheath segment of segments 88A, 88B of FIG. 6D, segments 92A, 92B, 92C, 92D of FIG. 6E, or segments 96A, 96B of FIG. 6F, for example), two sheath segments (such as two segments of segments 88A, 88B, segments 92A, 92B, 92C, 92D, or segments 96A, 96B, for example), or any other number of segments. In addition, it is also understood that the filler material can fill all sheath segments on a device.

In accordance with certain alternative implementations as will be described in further detail below, the one or more lumens (such as lumens 36A, 36B or 70A, 70B, 70C, 70D), including, for example, the lumens in the elongate members (such as lumens 56, 58 as shown in FIG. 5A), can be configured to receive a fluid (such as, for example, a contrast solution) such that the fluid can be urged from the proximal end to the distal end of the segment (such as segment 34 or 60) and thereby dispense or deliver the fluid out of the distal end of the segment.

There can be benefits of a proximal shaft having a lumen. As discussed above, it allows for transmission of fluid through a conduit that is smaller in diameter than the guiding catheter. In certain embodiments, the lumen is sized specifically to conduct the desired amount of a specific fluid into the distal tube, into an area proximal to the opening of the distal tube, into a wall of the distal tube, out of the wall of the distal tube through an opening somewhere along the length of the tube, or out of the distal end of the distal tube. The control of the lumen size can allow for transmission of more or less fluid, depending on what is desired. For example, less fluid can be desirable when the fluid is contrast solution that is typically used in several catheter-based procedures, because greater amounts of contrast solution can cause harm to the patient.

According to various embodiments, the manipulation shaft 16 can have a diameter that ranges from about 0.008 inches to about 0.07 inches. Alternatively, the shaft 16 can have a diameter that ranges from about 0.01 inches to about 0.04 inches. Further, the shaft 16 can have a size that ranges from about ¼ French to about 3 French. The various inner elongate members can be made of at least one metal and/or at least one polymer. The metal can be stainless steel, nitinol, or other similar metals. Specific examples of stainless steel include 304 or 316 grade stainless steel. In those embodiments with inner elongate members, the outer wall, sheath, or sheath segment of the shaft 16 is made of polymeric materials such as PET, PTFE, Teflon, FEP, PE, PEBA, or other similar materials.

The various manipulation shaft or sheath embodiments as discussed in further detail elsewhere herein provide for a gradual change in flexibility from the proximal end of the shaft to the distal end. Further, certain shaft implementations are configured such that the distal portion of the shaft couples with the distal tube in such a way as to maximize the inner diameter of the distal tube. That is, in certain implementations, the various catheter implementations disclosed or contemplated herein require a sufficiently accessible opening at the proximal end of the distal tube to allow for the lumen to be accessible for medical devices. In other words, the opening must be large enough and/or have sufficient clearance to allow for easy insertion of various medical devices into the opening such that the devices can be urged distally through the tube and out of the opening at the distal end of the tube. In certain of these embodiments, clearance at the opening at the proximal end of the distal tube can be optimized by minimizing the profile (by reducing the diameter, etc.) of the manipulation shaft according to various configurations as disclosed herein.

As mentioned above, in accordance with some embodiments, the distal portion of the manipulation shaft is integrated or embedded in the proximal end of the distal tube. For example, in certain implementations, the distal tube is molded over the distal end of the manipulation shaft, thereby creating a connection zone as discussed elsewhere herein.

Figure 12A:
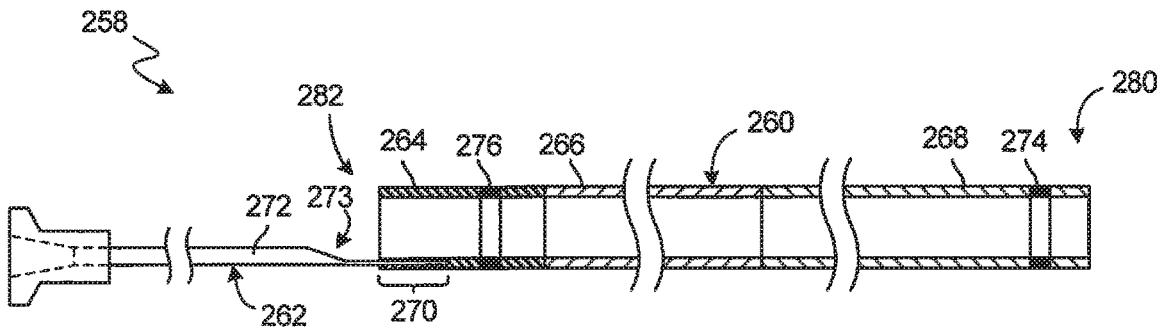
FIG. 12A is a side view in partial section of an extension catheter with two marker bands, according to one embodiment.
Figure 12B:
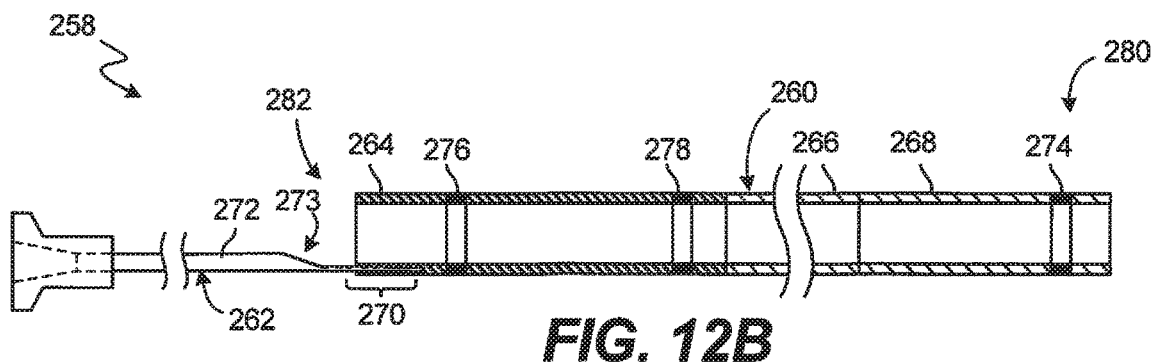
FIG. 12B is a side view in partial section of an extension catheter with three marker bands, according to another embodiment.
Figure 12C:
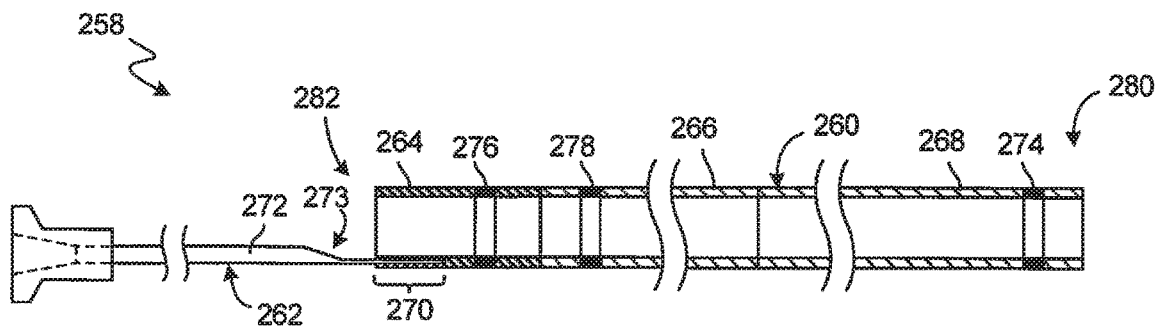
FIG. 12C is a side view in partial section of an extension catheter with three marker bands, according to a further embodiment.

Returning to FIG. 3A, the larger diameter distal tube 14 is, according to one embodiment, made generally from flexible polymeric materials. In certain implementations, the tube 14 is constructed with at least two layers. For example, the tube 14 can have two layers: a PEBAX, polyurethane, or NYLON outer layer, and a PTFE inner layer. Alternatively, the tube 14 can include a third polymeric layer (or more than three such layers). The tube 14 may also incorporate another layer comprised of re-inforcing coil or mesh. Such a coil or mesh layer can provide enhanced flexibility and/or strength. The tube 14 may also incorporate radiopaque markers (such as markers 274, 276, 278 as shown in FIGS. 12A-C and discussed below) on the tube 14. The manipulation shaft 16 may also incorporate one or more visual markers, including radiopaque markers.

The number and configuration of the elongate members and the one or more sheath segments (and any filler material positioned therein) in the manipulation shaft can influence the physical characteristics of the catheter. More specifically, these components can directly influence the torsional compliance characteristics of the device. It is understood that for purposes of this application, "torsional compliance" is intended to mean the angular or rotational flexibility of the shaft along its length. As an example, a shaft with high torsional compliance will transmit less torque or rotation from one end to the other end, while a shaft with low torsional compliance will transmit more torque from one end to the other. A shaft with low torsional compliance will have higher torque transmission charactistics than one with high torsional compliance. As discussed above, certain known extension catheters have high torque transmission characteristics (and thus low torsional compliance characteristics) that can cause sufficient stress on the connection between the proximal shaft and distal tube to cause failure or separation at the connection point. Non-limiting examples of extension catheters having low torsional compliance can include catheters having a proximal shaft comprised of a single elongate member having a solid square or rectangular cross-section, a solid round cross-section, or a round cross-section with a lumen (such as a hypotube).

In contrast, the use of two or more elongate members in combination with different sheath segment configurations can produce higher torsional compliance (and thus lower torque transmission) than proximal shafts that are not configured as such. More specifically, without being limited by theory, the capability of the two or more elongate members to move independently in relation to each other helps to increase torsional compliance/reduce torque transmission when the manipulation shaft is turned at its proximal end by the user to cause rotation of the distal tube or when torsion is induced in the shaft as a result of pushing (or pulling) the catheter through a guiding catheter and through a tortuous vessel. In a related fashion, a sheath segment that covers only a portion of the length of the elongate members (instead of the entire length thereof) also maintains some independent movement of the elongate members, thereby maintaining lower torque transmission in comparison to any configuration that includes a sheath that covers the entire length of the elongate members. In contrast, in those situations in which it is desirable, the addition of a filler material that acts as a bonding agent in one or more lumens of the sheath segment can decrease the torsional compliance characteristics (and thus increase the torque transmission characteristics), while a filler material that constitutes a lubricant can increase torsional compliance characteristics less than a bonding agent. As discussed above, the amount of filler can also influence the torsional compliance characteristics, including whether the filler fills the entire length of a sheath segment, a portion of the segment, more than one portion of the segment, or more than one segment.

Thus, it is understood that torsional compliance of any given device or shaft can be determined based on a number of factors, including the number and length of any sheath segments, the number and length of any unsheathed segments, the amount of filler, the type of filler, the cross-sectional shape of the two or more elongate members, the number of elongate members, and other known factors.

Figure 6A:
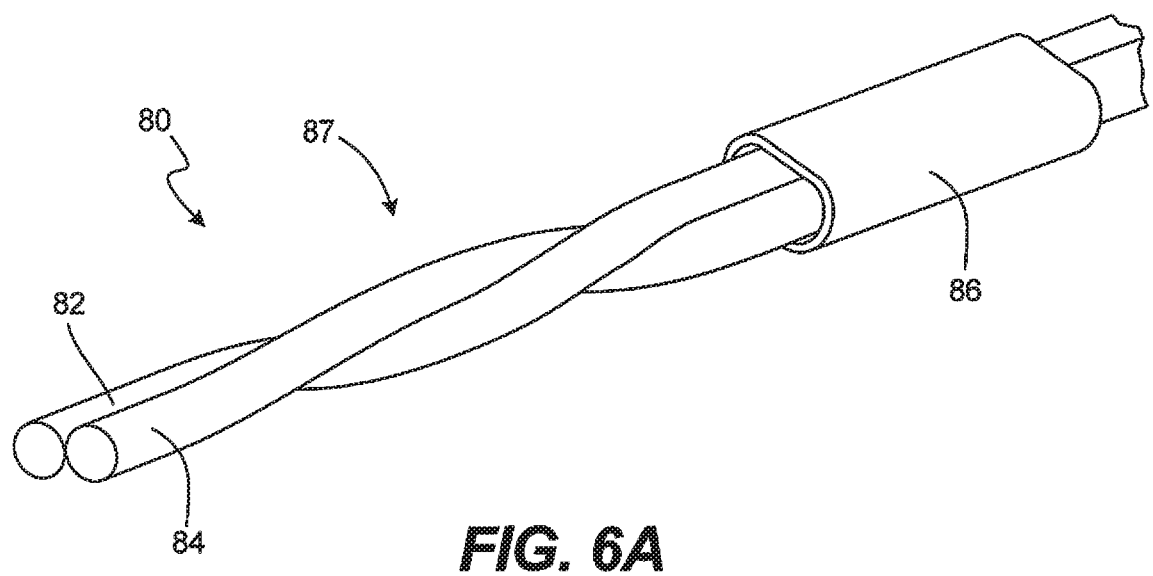
FIG. 6A is a perspective view of a proximal shaft of an extension catheter, according to one embodiment.

These concepts are best captured in FIG. 6A, which depicts a shaft 80 configuration with round rods 82, 84 having a sheath segment 86 and an unsheathed segment 87. The unsheathed segment 87 allows for the independent movement of two round elongate members 82, 84, thereby increasing torsional compliance as described above. That is, as shown by the fact that the proximal portions of the elongate members are wound together, the two elongate members can move independently in relation to each other—including being in sliding and rolling contact along their lengths—thereby increasing the torsional compliance of the shaft 80. In contrast, non-round elongate members would not be capable of rolling or rotating in relation to each other as easily, thereby resulting in decreased torsional compliance as a result of the contact between elongate members being merely slidable in nature (rather than both sliding and rolling/rotating). Further, the sheathed segment 86 reduces the amount of relative movement of the two rods 82, 84 such that their independent movement in relation to each other is more limited in comparison to the length of rods 82, 84 in the unsheathed segment 87, thereby resulting in decreased torsional compliance. Of course, it is understood that the two rods 82, 84 in the sheathed segment 86 can also be in sliding and rolling contact along their lengths, but it is also understood that the rods 82, 84 in the sheath 86 are not capable of rolling or rotating in relation to each other as easily as rods 82, 84 of an unsheathed segment (such as segment 87). And a filler injected into the segment 86 can further influence the torsional compliance as explained above.

Further, FIGS. 6B-6F depict various different additional manipulation shaft implementations, wherein each of the different configurations has a different impact on the torque transmission characteristics of the resulting device. More specifically, each of these figures shows a different embodiment of a manipulation shaft 80 having two elongate members 82, 84, with each embodiment having a different sheath segment configuration.

Figure 6B:
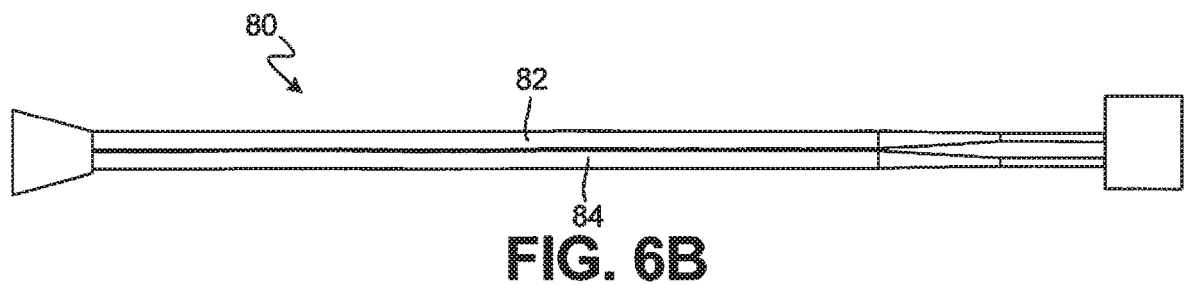
FIG. 6B is a top view of a proximal shaft of an extension catheter, according to another embodiment.

For example, FIG. 6B depicts a manipulation shaft 80 with the two elongate members 82, 84, but having no sheath segment. As described above, this shaft 80 would exhibit high torsional compliance (or low torque transmission) for the reasons set forth above.

Figure 6C:
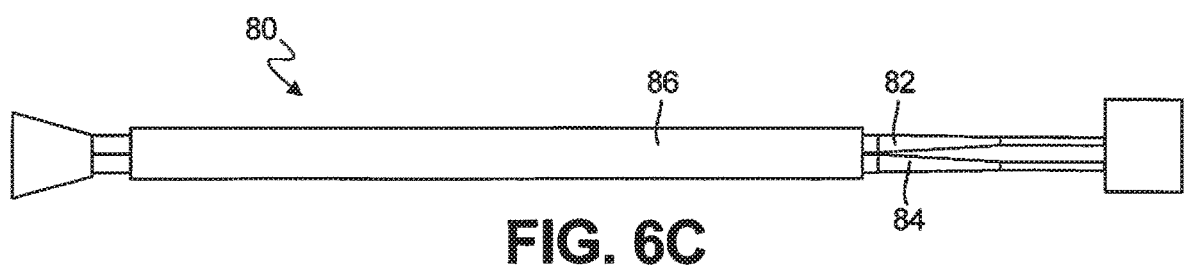
FIG. 6C is a top view of a proximal shaft of an extension catheter, according to a further embodiment.

FIG. 6C shows a manipulation shaft 80 with two elongate members 82, 84 and a sheath segment 86 that is disposed around the two elongate members 82, 84 for a substantial amount of the length of the members 82, 84. That is, the sheath segment 86 extends from a proximal portion of the members 82, 84 to a distal portion of the members 82, 84. In this embodiment, the shaft 80 exhibits lower torsional compliance characteristics than any of the other embodiments in FIGS. 6A-6F, because the sheath 86 is disposed around a greater length of the two members 82, 84 than any other embodiment, thereby limiting the freedom of the two members 82, 84 to move in relation to each other. Alternatively, the sheath segment 86 can be disposed around the elongate members 82, 84 for any length of those members 82, 84, including the entire length thereof. Further, as is true with any of the embodiments shown in FIGS. 6A-6F and elsewhere in this application, a bonding agent filler injected into the segment 86 will cause even lower torsional compliance characteristics (while a lubricant filler would have torsional compliance characteristics that are not as low as those created by a bonding agent).

Figure 6D:
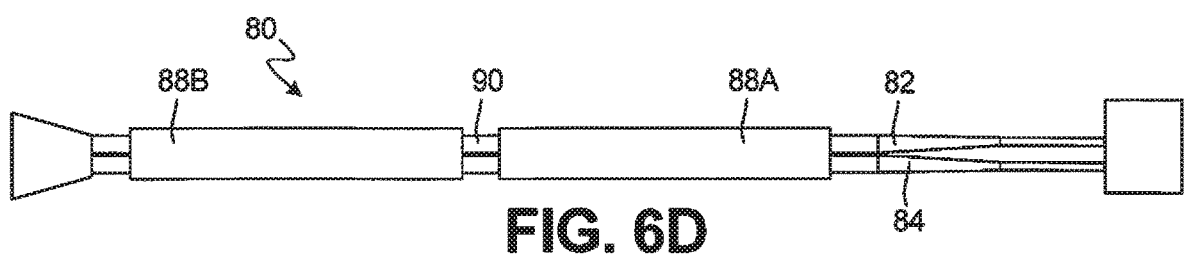
FIG. 6D is a top view of a proximal shaft of an extension catheter, according to yet another embodiment.
Figure 6E:
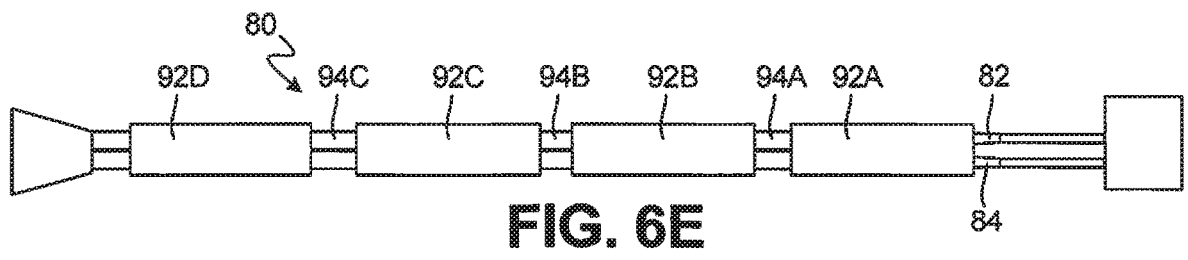
FIG. 6E is a top view of a proximal shaft of an extension catheter, according to a further embodiment.
Figure 6F:
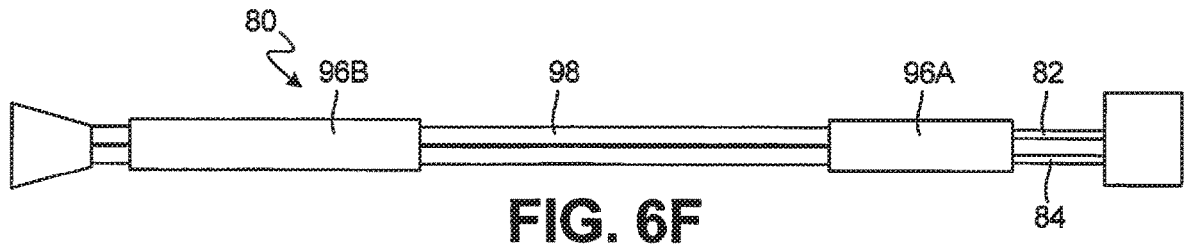
FIG. 6F is a top view of a proximal shaft of an extension catheter, according to another embodiment.

The manipulation shaft 80 embodiments in FIGS. 6D-6F all have at least two sheath segments disposed around two elongate members 82, 84. More specifically, FIG. 6D depicts a first or distal sheath segment 88A, and a second or proximal sheath segment 88B, with an unsheathed segment 90 between the two segments 88A, 88B. The shaft 80 in FIG. 6E has four sheath segments 92A, 92B, 92C, 92D with three unsheathed segments 94A, 94B, 94C disposed therebetween. Further, FIG. 6F has two sheath segments 96A, 96B with an unsheathed segment 98 between the two segments 96A, 96B. The unsheathed segment 98 in FIG. 6F has a greater length than the unsheathed segment 90 in FIG. 6D, which means that the shaft 80 in FIG. 6F exhibits lower torque transmission than the shaft 80 in FIG. 6D. In a further alternative, the shaft 80 can have a sheath that is disposed around the two elongate members 82, 84 and extends for the entire length of the shaft 80, thus constituting a unitary or non-segmented sheath. Further, it is understood that the sheath or segments can have any length and cover any portion of the length of the shafts. It is also understood that there can be any number of sheath segments or unsheathed segments. In addition, certain embodiments can have at least two segments that are disposed around the at least two elongate members and adjacent to each other such that they in contact with each other such that there are no unsheathed segments between the at least two segments.

Figure 6G:
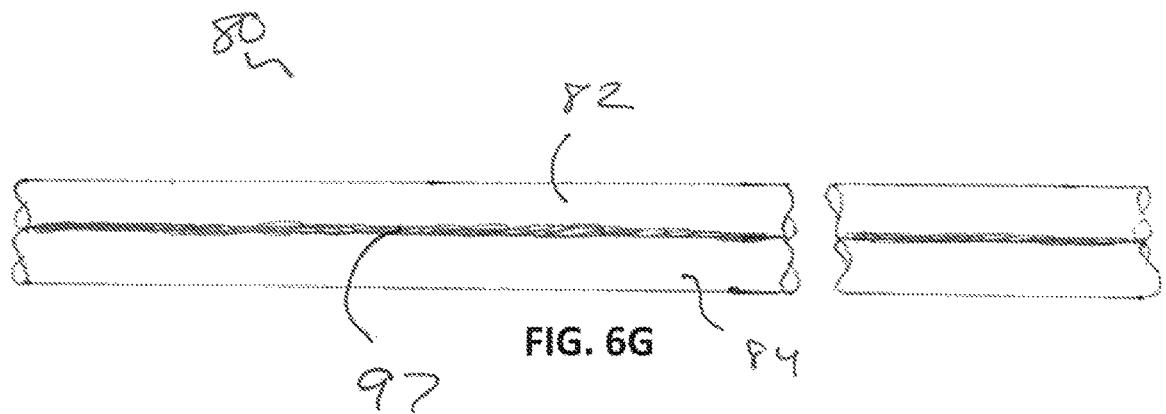
FIG. 6G is a top view of a proximal shaft of an extension catheter, according to another embodiment.
Figure 6H:
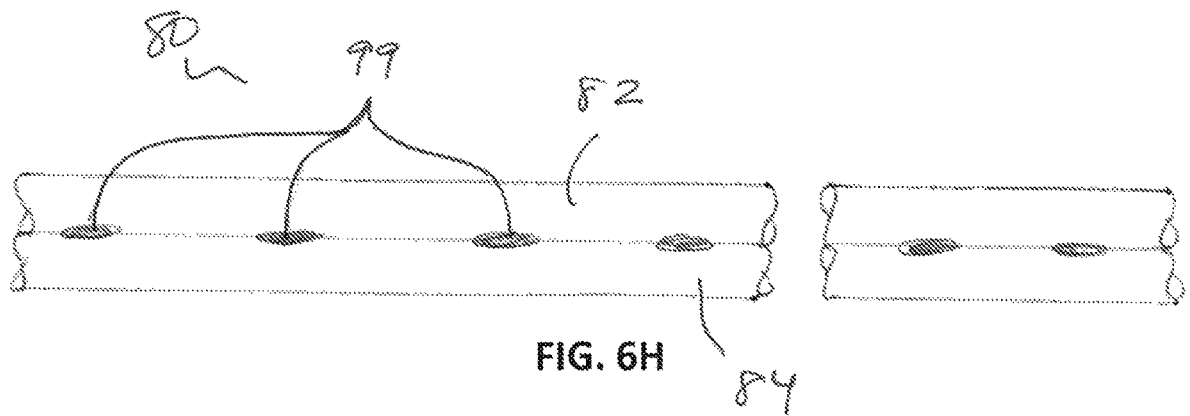
FIG. 6H is a top view of a proximal shaft of an extension catheter, according to another embodiment.

FIGS. 6G and 6H depict additional manipulation shaft 80 embodiments in which the two elongate members 82, 84 are welded or otherwise bonded or attached to each other. More specifically, FIG. 6G depicts the two elongate member 82, 84 bonded together at the binding 97 along the entire length of the members 82, 84 as shown. Alternatively, FIG. 6H depicts the two elongate members 82, 84 bonded together such that the bindings 99 are at predetermined discrete locations or sections along the length of the member 82, 84 such that only certain discrete portions of each member 82, 84 (at the bindings 99) are bonded together, while the remaining portions between those bindings 99 along the length of each member 82, 84 are not. In a further alternative, it is understood that any one or more portions of the two members 82, 84 that make up any portion of the length of the two members 82, 84 can be bonded together.

The elongate members 82, 84 can be joined at the binding (such as bindings 97 or 99) using welding or other similar known bonding or binding processes. For example, the joining or welding techniques can include (amongst other known binding processes): laser welding, spot welding, arc welding, tig welding, brazing, and other known joining processes. Some of these processes may involve adding an additional material. In other processes, the binding/filler material is the remelted/reflowed parent material (of the elongate members).

It is understood that the binding of the two elongate members 82, 84 together has the same, or similar, impact on the characteristics of the manipulation shaft 80 as the addition of a filler material that acts as a bonding agent as described above. That is, the binding of the member 82, 84 can decrease the torsional compliance characteristics (and thus increase the torque transmission characteristics). Further, as discussed above, the amount of the length of the two members 82, 84 that are bonded together can also influence the torsional compliance characteristics, including whether the two members 82, 84 are bonded together along the entire length of the members 82, 84, a portion of the length of the members 82, 84, or more than one discrete portion of the members 82, 84.

It is also understood that the binding of the two elongate members 82, 84 together can have a similar, but different, impact on the characteristics of the manipulation shaft 80 with respect to the contact between the two members 82, 84. That is, the binding of the two elongate members 82, 84 restricts the movement of the two members 82, 84 in relation to each other to some extent, but not entirely. In other words, while the movement of the two members 82, 84 is fully restricted at the bindings, the movement is not fully restricted along those lengths of the two members 82, 84 that are not bound together. Thus, it is understood that the binding of the two members 82, 84 still results in some movement of the two members 82, 84 in relation to each other. For example, the two members 82, 84 can still be twisted in relation to each other in some embodiments. Other relative movement between the two members 82, 84 is contemplated as well.

It is further understood that any binding of the two elongate members 82, 84 according to any embodiment or variation as described above and/or depicted in FIGS. 6G and 6H can be incorporated into any of the other device embodiments disclosed or contemplated elsewhere herein, including, but not limited to, those embodiments described herein having any sheath (or sheaths) of any kind and/or those embodiments having any filler material of any kind, and including, for example, the various embodiments depicted in FIGS. 5A-5N and described herein and other such implementations.

The two embodiments depicted in FIGS. 6G and 6H, and any variations thereof as disclosed or contemplated herein, can be incorporated into any of the other device embodiments disclosed or contemplated elsewhere herein. Thus, the two manipulation shaft 80 embodiments can be coupled to any of the device embodiments herein and can have one or more sheath segments disposed thereon according to any of the various embodiments herein.

Figure 7A:
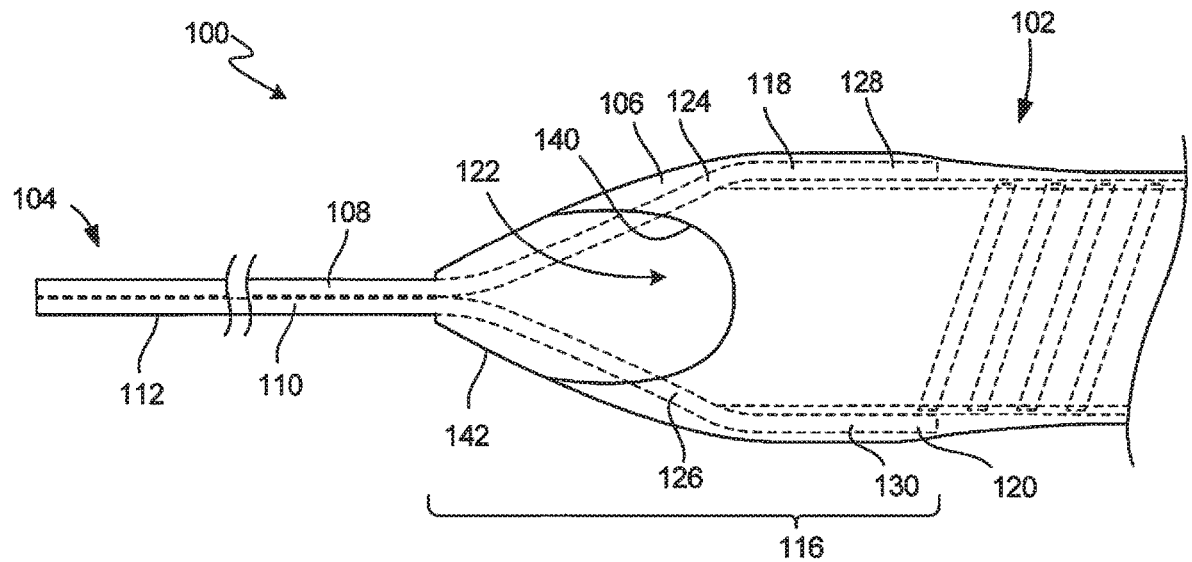
FIG. 7A is a top view of an extension catheter showing the junction of the proximal and distal portions, according to one implementation.
Figure 7B:
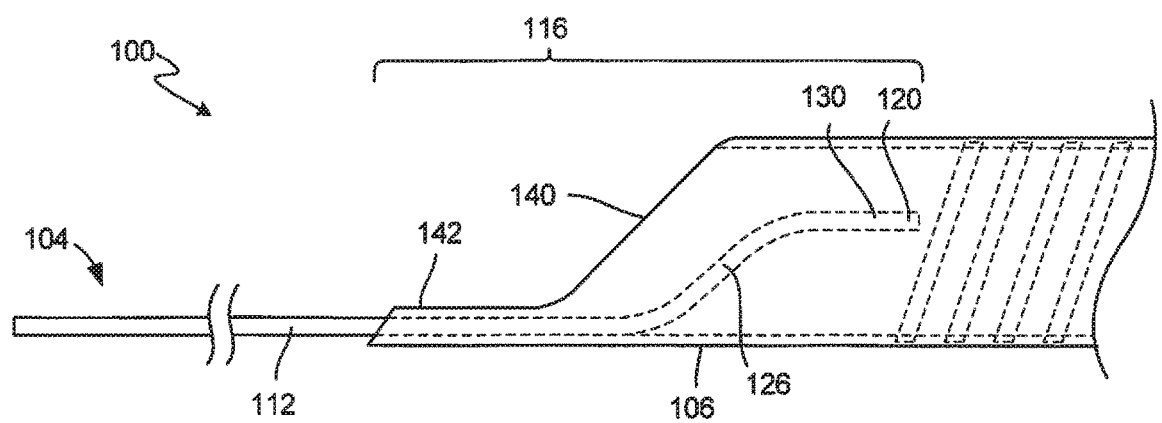
FIG. 7B is a side view of the extension catheter of FIG. 7A.
Figure 7C:
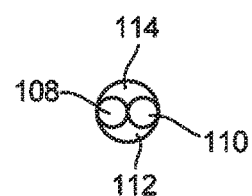
FIG. 7C is an end view of the proximal shaft of the extension catheter of FIG. 7A.

FIGS. 7A-7C depict another embodiment of a catheter 100 with a manipulation shaft 104 that is coupled to the distal tube 102 in an eccentric manner, rather than a concentric manner. That is, the shaft 104 is joined to the distal tube 102 at one point or in one zone of the periphery or circumference of the distal tube 102 or along an extension 142 of the distal tube 102 as discussed in further detail below. For example, in one implementation as shown in FIGS. 7A-7C, the manipulation shaft 104 is coupled to the distal tube 102 at a point or area of the wall 106 of the tube 102.

The shaft 104 in this embodiment is made up of two rods 108, 110 positioned within the lumen 114 of the sheath 112 disposed around the rods 108, 110, as best shown in FIG. 7C. In this embodiment, the rods 108, 110 are solid (that is, they do not have lumens). Alternatively, as discussed above, the rods 108, 110 can be hypotubes 108, 110, with each having a lumen defined therein, and/or can have a shape other than round.

As best shown in FIGS. 7A and 7B, this specific implementation has a distal portion of the shaft 104 that is similar to the configuration of FIG. 3A as discussed above, because the shaft 104 is coupled to and integral with the wall 106 of the distal tube 102 at the connection zone 116. Further, as best shown in FIG. 7A, like the device 10 in FIGS. 3A-3C, the two rods 108, 110 extend from the distal portion of the shaft 104 such that the distal portions 118, 120 of the rods 108, 110 extend into the distal tube 102. More specifically, the distal portions 118, 120 are positioned in the wall 106 contralaterally in relation to each other. That is, the distal portion 118 is disposed in the wall 106 on one side of the distal tube 102 while the distal portion 120 is disposed in the wall 106 on the other side of the tube 102 such that the portions 118, 120 are positioned across the lumen 122 from each other. As with every embodiment having contralateral distal portions, the distal portions 118, 120 can be directly opposite each other across the lumen 122, but in other implementations, they are not directly opposite each other.

Further, as best shown in FIG. 7B, both distal portions 118, 120 (only 120 is visible in FIG. 7B because of the location of distal portion 118 behind distal portion 120 in the figure) have angled portions 124, 126 that extend at an angle in relation to the longitudinal axis of the tube 102 and axial portions 128, 130 that extend axially along that position for some distance as well as shown. Alternatively, the distal portions 118, 120 can have only angled portions (similar to portions 124, 126) and no straight or axial portions. In accordance with one implementation, the positioning and configuration of the distal portions 118, 120 of the rods 108, 110 in the wall 106 of the distal tube 102 enhance the kink resistance of that portion of the tube 102 as well as assisting in more evenly transmitting an axial force to the distal tube 102 in a more even fashion during use of the catheter 100, while maintaining a low torque transmission.

In this specific implementation, both of the distal portions 118, 120 of the rods 108, 110 have a round configuration. Alternatively, they could have a flat configuration, thereby reducing their profiles within the distal tube 102.

In addition, in this implementation, as best shown in FIG. 7B, the distal tube 102 has a tapered proximal opening 140 and a proximal extension 142 that is configured to receive the manipulation shaft 104 as shown. In one implementation, the tapered proximal opening 140 provides easier access and insertion for any device being positioned through the lumen 122 of the distal tube 102, while the proximal extension 142 provides enhanced strength to the connection between the manipulation shaft 104 and the distal tube 102.

Figure 8A:
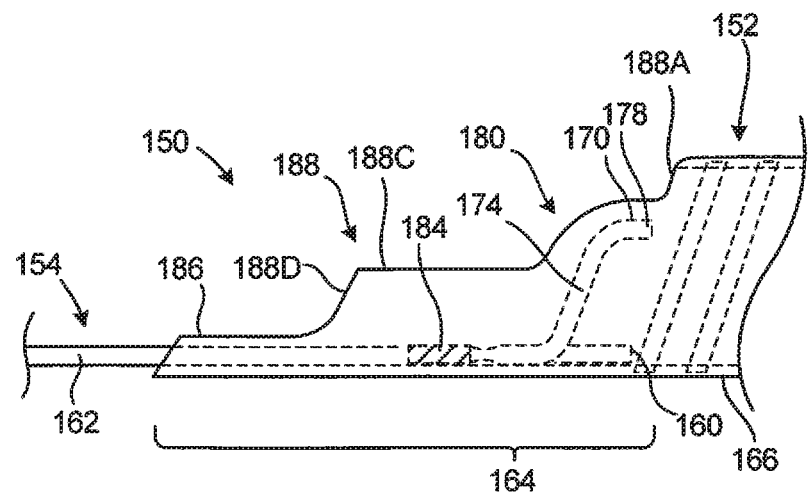
FIG. 8A is a side view of an extension catheter showing the junction of the proximal and distal portions, according to one implementation.
Figure 8B:
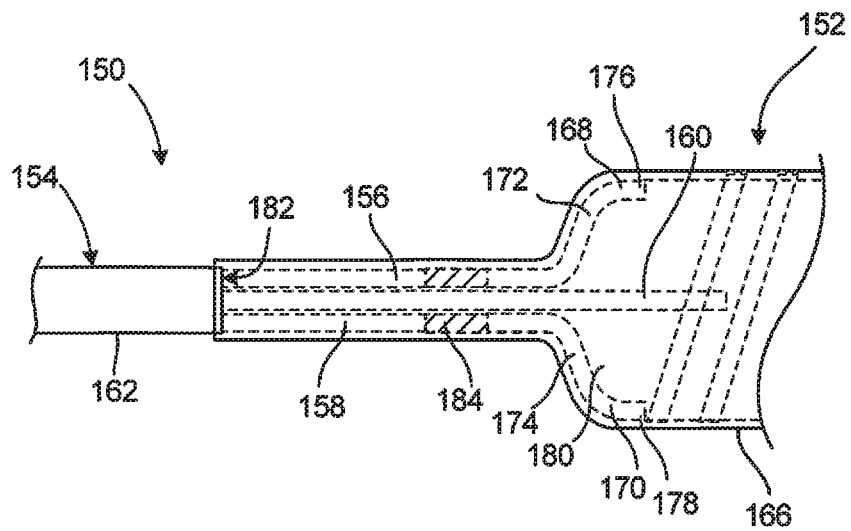
FIG. 8B is a top view of the extension catheter of FIG. 8A.

According to a further embodiment depicted in FIGS. 8A and 8B, the device 150 has a manipulation shaft 154 that is made up of two rods 156, 158 and a tube 160 positioned between the two rods 156, 158 (as best shown in FIG. 8B). FIG. 8A is a side view, while FIG. 8B is a top view. In this implementation, the shaft 154 has a polymeric sheath segment 162 such as polyester and/or PET that is disposed around the two rods 156, 158 and tube 160. A distal portion of the shaft 154 is coupled to and integral with an outer wall 166 of the distal tube 152 at the connection zone 164, and more specifically is coupled to a proximal extension 186 of the tube 152. Further, the two rods 156, 158 extend distally such that the distal portions 168, 170 of the rods 156, 158 extend into the distal tube 152. The distal portions 168, 170 are positioned in the wall 166 contralaterally in relation to each other. That is, the distal portion 168 is disposed in the wall 166 on one side of the tube 152 while the distal portion 170 is disposed in the wall 166 on the other side of the tube 152 such that the portions 168, 170 are positioned across the lumen 180 from each other. Further, as best shown in FIG. 8A, both distal portions 168, 170 (only 170 is visible in FIG. 8A because of the location of distal portion 168 behind distal portion 170 in the figure) have angled portions 172, 174 that extend at an angle in relation to the longitudinal axis of the tube 152 and axial portions 176, 178 that extend axially along that position for some distance as well as shown. In this specific implementation, both of the distal portions 168, 170 of the rods 156, 158 have a round configuration. Alternatively, they could have a flat configuration, thereby reducing their profiles within the distal tube 152.

In addition, in this implementation, the tube 160 positioned between the two rods 156, 158 has a proximal end of the tube 160 extending proximally of the distal tube 152 and the distal end extending into the distal tube 152 as shown. It is understood that the proximal end of the tube 160 can be positioned at any point along the length of the manipulation shaft 154. Alternatively, the proximal end of the tube 160 can extend to the proximal end of the manipulation shaft 154. According to one embodiment, the tube 160 has a lumen (not shown) in fluid communication with the lumen 182 of the sheath segment 162 and further in fluid communication with the lumen 180 of the distal tube 152. Alternatively, the tube 160 can have a lumen (not shown) that is not in fluid communication with the lumen 182 or the lumen 180. In yet another alternative, the tube 160 has no lumen. Further, in this embodiment, two marker bands 184 are positioned around the rods 156, 158.

As mentioned above, in this embodiment, the tube 160 extends distally into the distal tube 152 such that the lumen (not shown) of the tube 160 is in fluid communication with the lumen 180 of the distal tube 152. Alternatively, the tube 160 extends distally out of the sheath 162 such that the distal end of the tube 160 is positioned in the tapered opening 188 of the distal tube 152 (described in further detail below). In that embodiment, the lumen is in fluid communication with an area external to and proximal to the lumen 180 of the distal tube 152. In a further alternative, the tube 160 can extend distally to or beyond the distal end of the distal tube 152 such that the lumen (not shown) of the tube 160 is in fluid communication with an area external to and distal to the distal tube 152. In a further embodiment.

In addition, in this implementation (like the embodiment depicted in FIGS. 7A and 7B), as best shown in FIG. 8A, the distal tube 152 has a proximal extension 186 configured to receive the manipulation shaft 104 as shown and a tapered proximal opening 188. The tapered proximal opening 188 in this embodiment has levels of tapering as shown, including a sharp tapered portion 188A, a curved tapered portion 188B, an axial portion 188C, and a second sharp tapered portion 188D. The tapered opening 188 provides easier access and insertion for any device being positioned through the lumen 180 of the distal tube 152, while the proximal extension 186 provides enhanced strength to the connection between the manipulation shaft 154 and the distal tube 152.

Figure 9A:
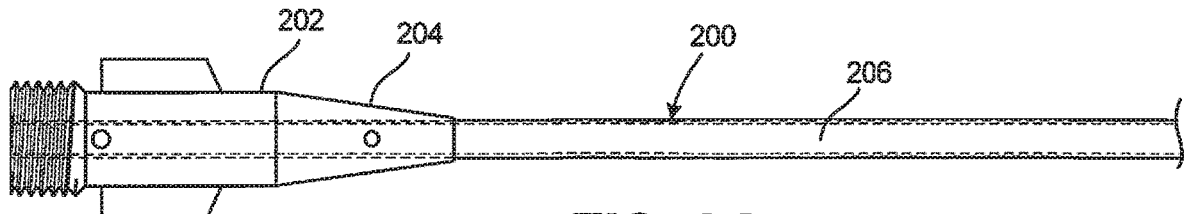
FIG. 9A is a cross-sectional side view of a proximal shaft of an extension catheter, according to one embodiment.

As shown in FIG. 9A, according to certain implementations, a manipulation shaft 200 can terminate in a proximal fitting 202. In accordance with one embodiment, the fitting 202 is adapted for connection to a fluid source. In certain embodiments, the fitting 202 is a standard female luer connection that is made from plastic. The fitting 202 can be bonded to the manipulation shaft 200 with adhesive, or it can be insert-molded over the manipulation shaft 200. In the embodiment shown in FIG. 9A, there is an optional strain-relief segment 204 disposed between the manipulation shaft 200 and the proximal fitting 202. The strain relief segment 204 provides a flexible transition from the manipulation shaft 200 to the proximal fitting 202. In this embodiment, the lumen 206 of the shaft 200 extends through the proximal fitting 202 as shown.

Figure 9B:
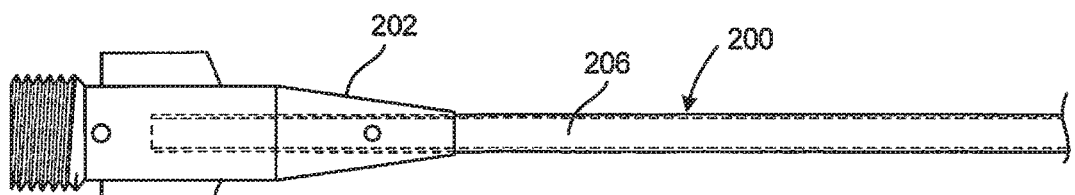
FIG. 9B is a cross-sectional side view of a proximal shaft of another extension catheter, according to a further embodiment.

Alternatively, in FIG. 9B, the proximal end of the lumen 206 in the shaft 200 does not have an opening. That is, the proximal end of the lumen 206 is not in fluid communication with any opening at the proximal end of the shaft 200.

Figure 10:
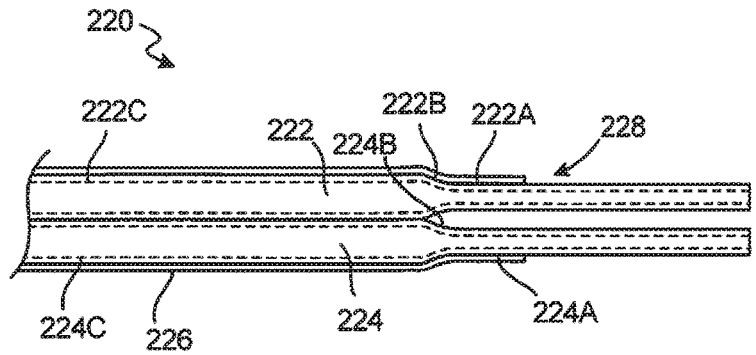
FIG. 10 is a cross-sectional top view of a proximal shaft of an extension catheter, according to one embodiment.

As discussed above, certain proximal shaft implementations have a sheath defining a lumen in which two separate inner elongate members are positioned. For example, the manipulation shaft 220 shown in FIG. 10 has a sheath 226 defining a lumen 228 with two inner elongate members 222, 224 positioned therein, wherein each of the elongate members 222, 224 have lumens. In this embodiment, both of the elongate members 222, 224 have reduced diameter portions 222A, 224A as shown. In this exemplary embodiment, each elongate member 222, 224 has a connection section 222B, 224B between the full diameter section 222C, 224C and the reduced diameter section 222A, 224A that involves a narrowing or neck around the full circumference of the members 222, 224 as shown.

Figure 11:
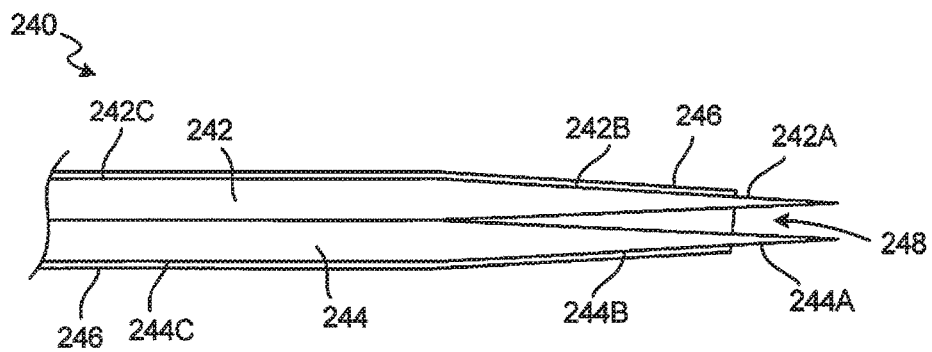
FIG. 11 is a cross-sectional top view of a proximal shaft of an extension catheter, according to another embodiment.

Alternatively, the manipulation shaft 240 shown in FIG. 11 has sheath 246 defining a lumen 248 with two inner elongate members 242, 244 positioned therein. The sheath 240 has a tapered section 246 in which both of the elongate members 242, 244 have tapered sections 242B, 244B as shown. In this exemplary embodiment, each elongate member 242, 244 has an extended taper from the full diameter section 242C, 244C to the reduced diameter section 242A, 244A.

As shown in FIGS. 12A-12C, certain embodiments of a distal tube 260 can have three segments or more of differing flexibilities: low flexibility at the proximal end 264 of the tube 260, medium flexibility in the middle 266 of the tube 260, and high flexibility at the distal end 268. More segments of varying flexibilities can also be used. In fact, the connection zone 270 (the area of overlap in which the manipulation shaft 262 is coupled to the larger tube 260) has varying flexibility in that zone 270. The differing flexibilities can be accomplished through combinations of differing materials, configurations, or geometries—as is known in the art (e.g. mesh or coil reinforcing, different PEBAX varieties, etc.). Moreover, different lengths can be selected for the segments 264, 266, 268 and the connection zone 270 according to design considerations. This permits more flexibility along a greater length of the device 258 as needed to deal with anticipated curvature in the path the catheter 258 must follow. In another implementation, the at least three segments have differing flexibilities as follows: low flexibility at the proximal end 264, high flexibility in the middle 266, and low flexibility at the distal end 268. Any other combination of flexibilities is also possible.

As mentioned above, the flexible tube 260 can have radiopaque markers embedded in the tube 260 and/or placed along the length of the tube 260 for various purposes. For example, marker 274 can be used at or near the distal tip 280 of the tube 260 to help the doctor locate the position of the tip 280. Another marker 276 could be used at or near the proximal end 282 of the tube 260 to assist the doctor in locating that end 282 of the tube 260 relative to the end of the guiding catheter or to assist in visualizing the location of the proximal opening of the tube 260. In one embodiment, the marker band 276 can be located near the proximal end 282 of the tube but at a position on the tube 260 that is distal to the end 282, as shown in FIGS. 12A-12C.

Further, in certain embodiments, a radiopaque marker (not shown) can be located anywhere in or near the connection zone 270 (e.g. on the manipulation shaft 262 in or near the connection zone 270 or in the distal tube 260 in the connection zone 270). Further, any of the markers 274, 276, 278 can be non-cylindrical. For example, one or more of the markers 274, 276, 278 can be strips or other known configurations.

One or more of these markers 274, 276, 278 can be helpful to indicate to the doctor or surgeon the location of the proximal end 282 of the tube 260 in relation to the guiding catheter (not shown) so that they do not insert or push the proximal end 282 past the distal end of the guiding catheter.

In this regard, certain embodiments include a third marker 278 located at some optimal point along the tube 260 in between the other two markers 274 and 276, as shown in FIGS. 2B, 12B, and 12C. As best shown in FIG. 2B, the doctor or surgeon can use this third marker 278 to track how far the tube 260 is extending beyond the guiding catheter 12. That is, the third marker 278 can be used in certain circumstances as a limit indicator. For example, in a specific embodiment having a tube 260 that is 35 cm in length, the third marker band 278 may be located 15 cm from the distal end 280 of the tube 260 in order to indicate this predetermined distance to the doctor, such that the doctor knows the distance that the distal end 280 extends beyond the guide catheter 12. Depending on the specific configuration of the catheter 258, the third marker band 278 can be disposed in the low flexibility segment 264, the middle flexibility segment 266, or possibly even in the high flexibility segment 268.

It is understood that the distal tube 260 can have one, two, three, or more markers as described above. It is further understood that any marker arrangement of one or more markers, including the three marker arrangement, can be used in connection with a variety of catheter configurations, including those having a solid rail (e.g. a flat or round wire) or a hollow rail or proximal section with a lumen, such as a tube. In other implementations, one or more markers can be positioned on the manipulation shaft 262.

In further embodiments, the proximal shaft 262 can have greater longitudinal flexibility than the distal tube 260 or any portion thereof.

According to certain implementations, the proximal shaft 262 can have a lumen 272 that extends along the length of the proximal shaft 262. As shown, the lumen 272 has an distal opening 273 that is in fluid communication with an area external to and proximal to the distal tube 260. In alternative embodiments, the shaft 262 can extend distally into the distal tube 260 such that the lumen 272 is in fluid communication with the lumen of the distal tube 260 via the opening 273. In a further alternative, the shaft 262 can extend distally through the distal tube 260 such that the lumen is in fluid communication with an area external to and distal to the distal tube 260. In yet another alternative, the proximal shaft 262 has no lumen.

Figure 13A:
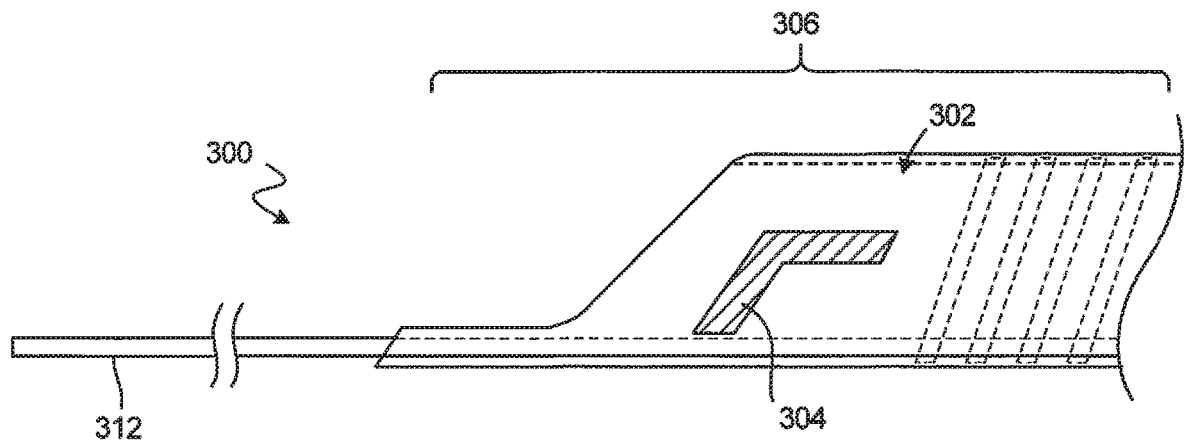
FIG. 13A is a cross-sectional side view of an extension catheter showing the junction of the proximal and distal portions, according to one implementation.
Figure 13B:
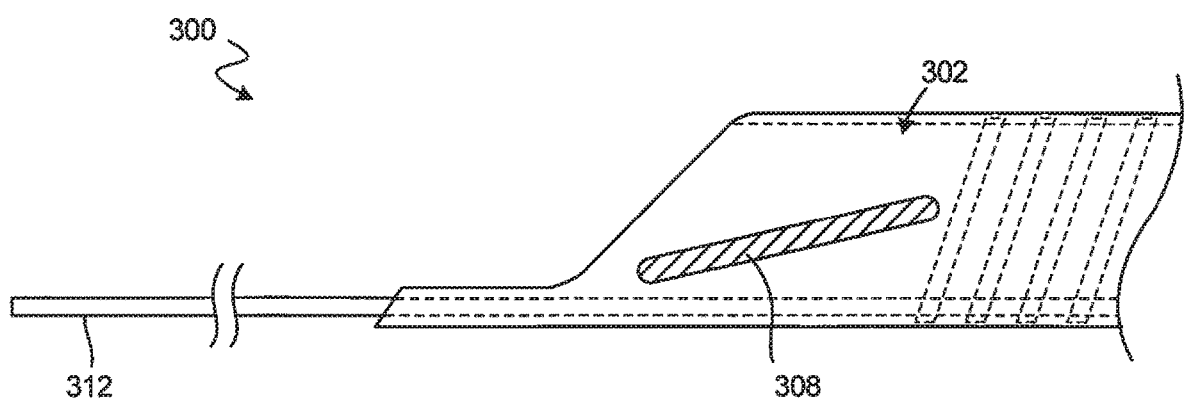
FIG. 13B is a cross-sectional side view of an extension catheter showing the junction of the proximal and distal portions, according to another implementation.
Figure 13C:
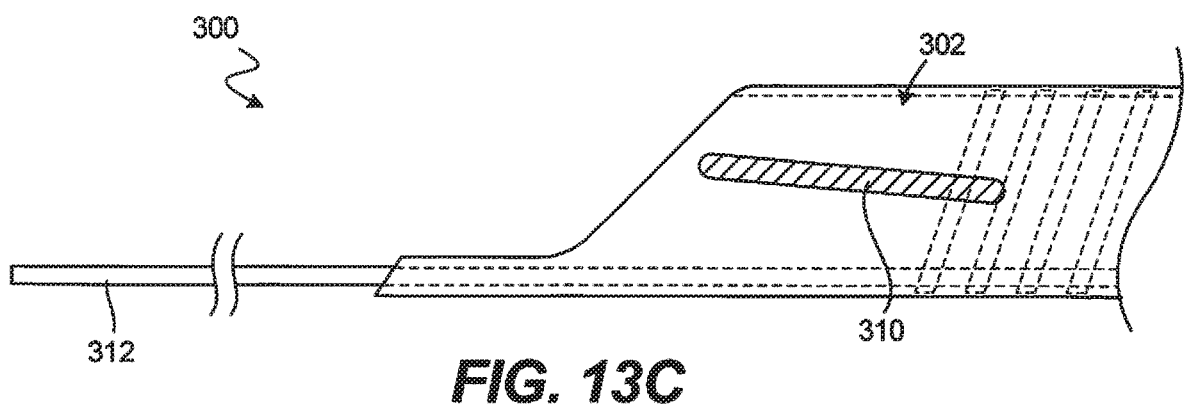
FIG. 13C is a cross-sectional side view of an extension catheter showing the junction of the proximal and distal portions, according to a further implementation.
Figure 14A:
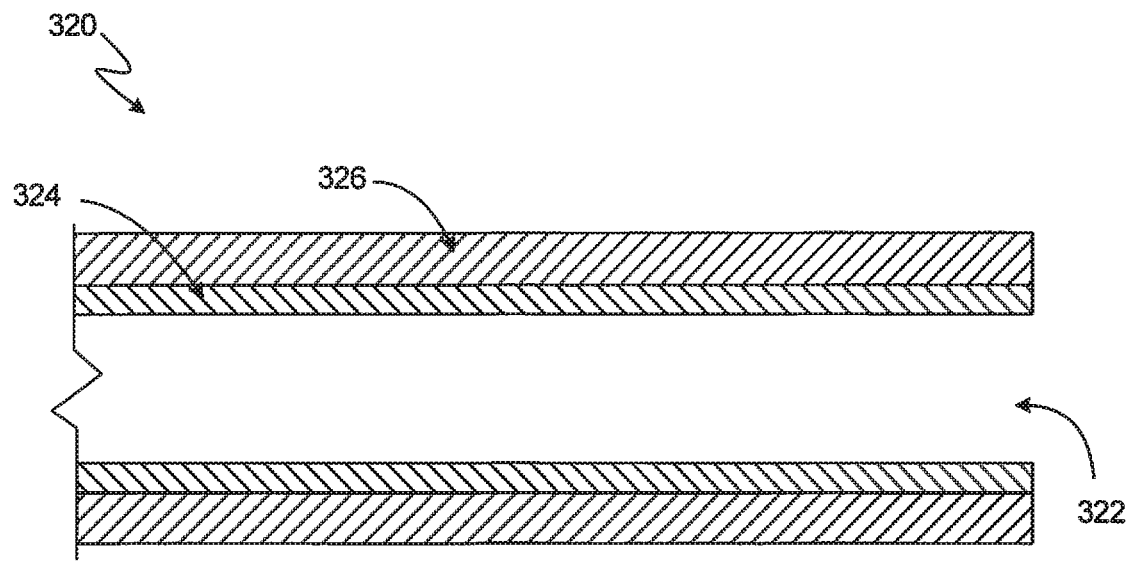
FIG. 14A is a cross-sectional view of a distal end of a standard multi-layer catheter.
Figure 14B:
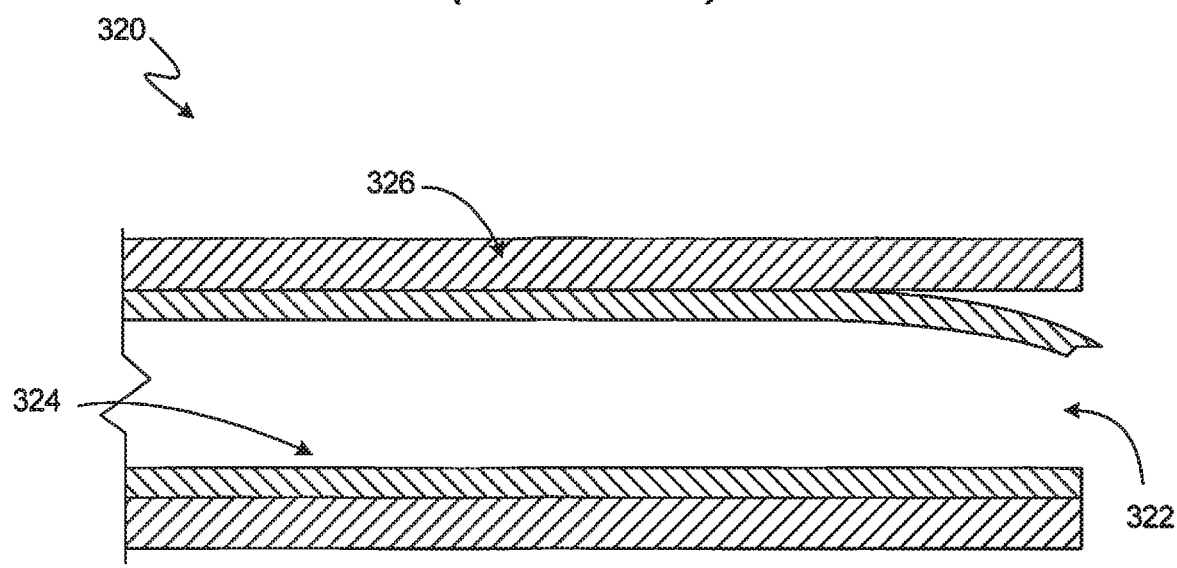
FIG. 14B is another cross-sectional view of the distal end of the standard multi-layer catheter of FIG. 14B.

Other embodiments include additional support structure in the distal tube that can provide mechanical advantage similar to that provided by the support coil. FIG. 13A depicts a device 300 having a distal tube 302 with a support member 304 positioned in the connection zone 306 that is configured to assume at least some of the mechanical loads. Alternatively, FIG. 13B depicts another embodiment of a support member 308 positioned in the connection zone 306 of a distal tube 302, while FIG. 13C shows a further implementation of a support member 310. In a further alternative, the tube 302 can have two or more support members. In certain embodiments, the support member (including the support members 304, 308, 310 depicted in FIGS. 13A-13C) can be the distal portion of the rod or tube extending distally from the shaft 312.

As mentioned above, certain additional embodiments as disclosed and contemplated herein relate to an improved catheter tip that can be incorporated into any known multilayer catheter, including any catheter disclosed herein or any other catheter for use in a human patient. As will be explained in further detail below, the various catheter tip embodiments disclosed herein have a protective wrap disposed at the tip of the catheter that eliminates any exposed ends of the tubular layers.

Figure 15:
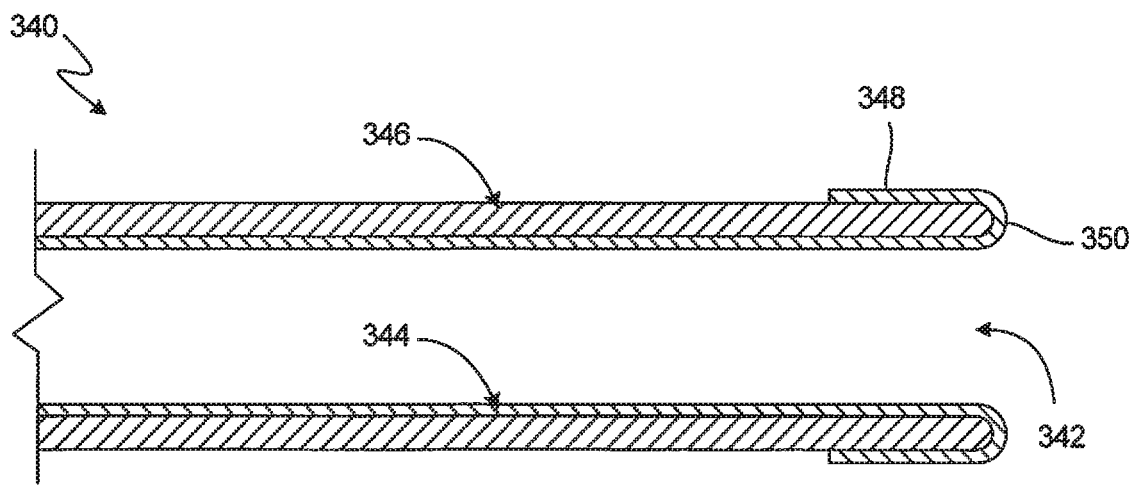
FIG. 15 is a cross-sectional view of a distal end of a multi-layer catheter with a protective wrap, according to one embodiment.

One embodiment of catheter tube 340 with an improved catheter tip 342 is depicted in FIG. 15. The tube 340 has a first layer (which, in this example, is also an inner layer) 344 and a second layer (which, in this example, is also an outer layer) 346. The two layers 344, 346 are positioned adjacent to each other and are adhered, coupled, or otherwise attached to each other along a substantial length of each. The inner layer 344 also has a protective wrap (also referred to as an "extended portion," "extension," "distal wrap," or "protective tip") 348 that extends beyond the length of the outer layer 346 and, in this implementation, is wrapped around the distal end of the outer layer 346 such that the external portion (also referred to as "outer portion" or "distal portion") of the extended portion 348 extends toward the proximal end of the tube 340 and is positioned against or adjacent to the exterior surface of the outer layer 346. This configuration creates a fold 350 (also referred to herein as a "distal fold") of the extended portion 348 at the catheter tip 342 that facilitates protection of the tube layers at the tip 342. In other words, the positioning of the extended portion 348 as shown ensures that the ends of the layers 344, 346 are not exposed at the distal end of the tube 340, thereby reducing the risk of delamination and the problems related thereto.

In this particular embodiment, the protective wrap 348 is integral with and is an extended portion of the inner layer 344. Alternatively, in any of the catheter tip embodiments disclosed or contemplated herein, the protective wrap (such as protective wrap 348) can be a separate component that is coupled to the distal ends of the inner layer (in this example, the inner layer 344) and the outer layer (in this case, the outer layer 346). In a further alternative, in any of the catheter tip embodiments disclosed or contemplated herein, the protective wrap (such as protective wrap 348) can be integral with and an extended portion of the outer layer (such as outer layer 346).

Figure 16:
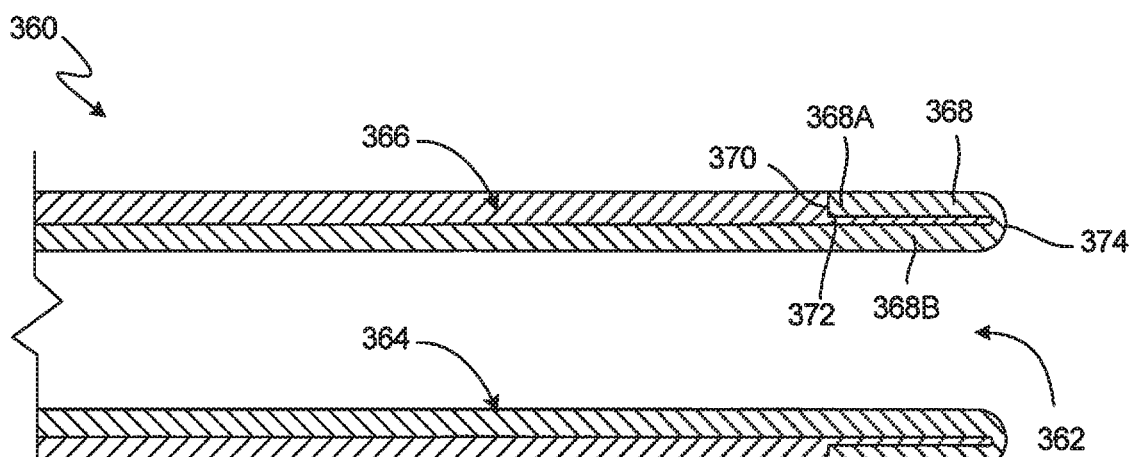
FIG. 16 is a cross-sectional view of a distal end of a multi-layer catheter with a protective wrap, according to another embodiment.

FIG. 16 shows another embodiment of a catheter tube 360 with an improved catheter tip 362. The tube 360 has a first (or "inner") layer 364 and a second (outer) layer 366 that are positioned adjacent to each other and are attached to each other along a substantial length thereof. In this implementation, the protective wrap 368 is an extended portion 368 of the inner layer 364 that extends beyond the length of the outer layer 366 and, in this implementation, is folded such that the external portion or outer portion (also referred to herein as the "distal portion") 368A of the extended portion 368 is positioned against or adjacent to the internal portion or inner portion (also referred to herein as the "proximal portion") 368B and the distal end 370 of the external portion 368A is positioned against or attached to the distal end 372 of the outer layer 366. This configuration creates a fold 374 (also referred to herein as a "distal fold") of the extended portion 368 at the catheter tip 362 that facilitates protection of the tube layers at the tip 362. Like the embodiment depicted in FIG. 15, the configuration of the protective wrap 368 as shown ensures that the ends of the layers 364, 366 are not exposed at the distal end of the tube 360, thereby reducing the risk of delamination and the problems related thereto.

Figure 17:
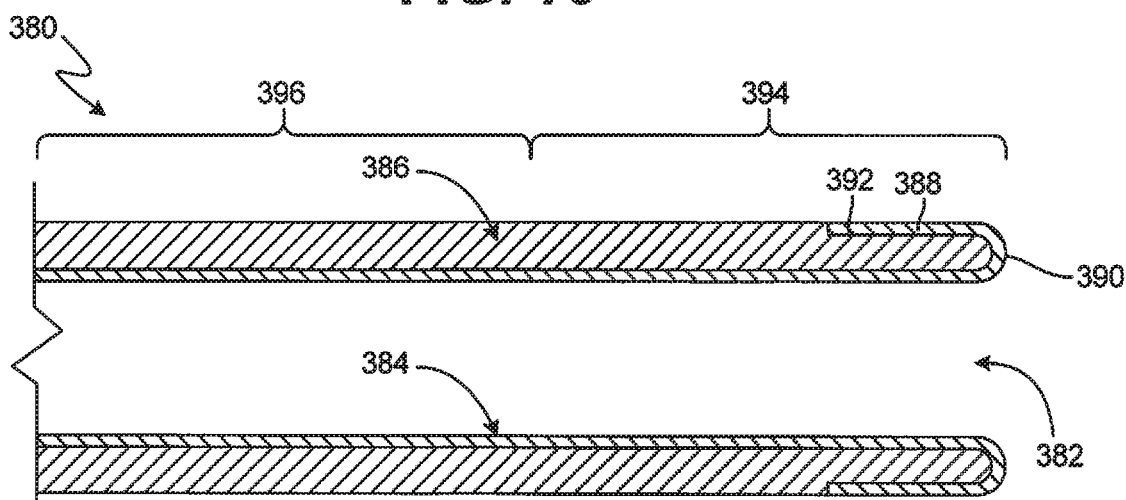
FIG. 17 is a cross-sectional view of a distal end of a multi-layer catheter with a protective wrap, according to a further embodiment.

A further implementation of a catheter tube 380 with an improved catheter tip 382 is depicted in FIG. 17. The tube 380 has a first (inner) layer 384 and a second (outer) layer 386 that are are positioned adjacent to each other and are attached to each other along a substantial length thereof. The protective wrap 388 in this embodiment is an extended portion 388 of the inner layer 384 that extends beyond the length of the outer layer 386 and, in this implementation, is wrapped around the distal end of the outer layer 386 such that the external portion of the extended portion 388 extends toward the proximal end of the tube 380 and is positioned against or adjacent to the exterior surface of the outer layer 386. This configuration creates a fold 390 (also referred to herein as a "distal fold") of the extended portion 388 at the catheter tip 382 that facilitates protection of the tube layers at the tip 382. However, unlike the embodiment in FIG. 15, in this implementation, the external portion of the extended portion 388 is positioned in a recess 392 or other type of configuration formed or defined in the external surface of the outer layer 386 such that the external portion of the extended portion 388 is "flush" with the outer layer 386. In other words, the external portion of the extended portion 388 is positioned in the recess 392 such that the external diameter of the tube 380 along the length in which the external portion of the extended portion 388 is positioned in the recess 392 is the same as (or similar to) the external diameter along the length made up solely of the inner 384 and outer layers 386.

In an alternative implementation, the recess (such as recess 392) can be created by a third layer (not shown), which is an additional outer layer that is external to the outer layer 386 and is positioned to create the recess 392. In other words, in this alternative, the layer 386 as shown in FIG. 17 is no longer an outer layer but instead is a middle layer that has no recess defined therein. Instead, the third layer is positioned over the middle layer but is shorter than the middle layer, thus leaving a portion of the middle layer exposed near the distal end, thereby creating the recess 392.

In this embodiment of FIG. 17, the placement or disposition of the external portion of the protective wrap 388 in the recess 392 can create a smooth (also referred to as "non-catching" or "non-snagging") outer surface of the tube 380 that reduces or prevents the occurrence of friction or snagging of the outer surface of the tube 380 within a mating (telescopic) second catheter or within a lumen or blood vessel in a patient during advancement or retraction of the tube 380. In other words, the smooth outer surface means that there is no catch point formed by the protective wrap 388 that could potentially cause difficulties or damage in advancing or removing the device in relation to a patient.

In accordance with a further implementation, any of the improved catheter tips as discussed above with respect to FIGS. 15-17 or contemplated elsewhere herein can also have variable stiffnesses along the length of the tip. For example, as shown with respect to FIG. 17, in some embodiments, a distal portion 394 of the distal end of the tube 380 can be relatively stiffer than a proximal portion 396 of the distal end of the tube 380. In certain specific implementations, the greater stiffness of the distal portion 394 is caused by the composition or materials of the distal portion 394 having a higher durometer than the composition or materials of the proximal portion 396. Alternatively, the greater stiffness of the distal portion 394 can be accomplished in any known fashion. It is understood that the length of the tube 380 that is considered the distal portion 394 (and thus the proximal portion 396) can vary, and that the specific lengths depicted in FIG. 17 are merely exemplary.

One of ordinary skill in the art would understand that any of the above multi-layer catheter embodiments or any other embodiments contemplated herein can have more than two layers. For example, in certain implementations, the catheter can have 3 layers. Alternatively, the catheter can have 4 layers. In further embodiments, the catheter can have 5 or more layers.

It is further understood that the tubes of the multi-layer catheter embodiments can be made of one or more additional known polymeric, metal, or other materials that are typically used in catheters. Further, any tube embodiment can also include one or more radioopaque markers, including the examples described in further detail below. Further, the various tube implementations can also include a metal braid or coil configuration in the tube for additional reinforcement.

As discussed above, it is also understood that the catheter tip embodiments disclosed or contemplated herein can be incorporated into any known multi-layer catheter devices. For example, in one implementation, a catheter tip embodiment could be incorporated into a guiding catheter, including, for example, the guiding catheter 12 depicted in FIG. 1 and discussed above. Alternatively, any of the catheter tip embodiments can be incorporated into any extension catheter such as those extension catheter embodiments disclosed or contemplated elsewhere herein. For example, any of the catheter tip embodiments disclosed or contemplated herein can be incorporated into the boosting catheter 10 as shown in FIGS. 2A and 2B, the extension catheters depicted in FIGS. 3A-3C and FIGS. 4A-4B, catheters having various manipulation shaft implementations such as those depicted in FIGS. 6A-6F, and the boosting catheters 258 of FIGS. 12A-12C, and any other catheter embodiments disclosed or contemplated herein. In addition, the various catheter tip embodiments disclosed herein can also be integrated into or combined with any known catheter. Further, it is understood that any of the improved catheter tip embodiments disclosed or contemplated herein can be integrated into or combined into a distal tip, including the distal end of any distal tube, of any of the various catheter implementations, such as guiding catheters, sheaths, delivery catheters (including stent delivery systems), snares, and arthorectomy catheters.

Further, it is understood that any of the various improved catheter tip embodiments disclosed or contemplated herein can be integrated into or combined with any boosting catheter, including the boosting catheter disclosed and claimed in U.S. application Ser. No. 14/210,572, entitled "Boosting Catheter and Related Systems and Methods," which is hereby incorporated herein by reference in its entirety.

In addition, any of the various catheter embodiments disclosed herein, including the various implementations having a segmented catheter structure and the various implementations having an improved catheter tip can have an external lubricious coating. The external lubricious coating can be positioned around or integral with an entire length of the distal tube (or any portion thereof), an entire length of the proximal shaft (or any portion thereof), or an entire length of both the distal tube and the proximal shaft (or any portions thereof). In some implementations, the lubricious coating can be hydrophobic, while in other embodiments it can be hydrophilic.

Figure 18:
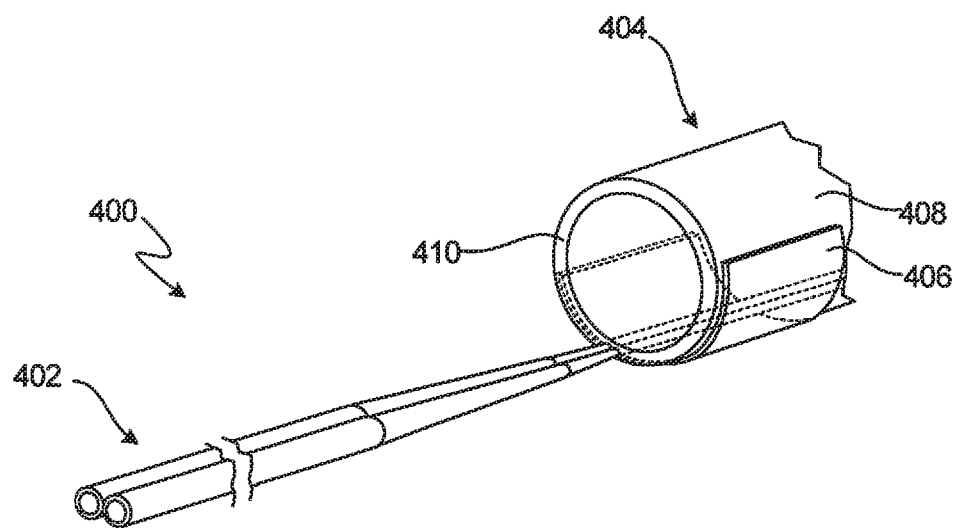
FIG. 18 is a perspective view of a portion of a catheter with a support membrane, according to one embodiment.

Further, any of the various catheter embodiments disclosed herein, including the various implementations having a discontinuous or segmented catheter structure and the various implementations having an improved catheter tip, can also have an outer support membrane (also referred to as a "support membrane" or "support layer") disposed around a proximal portion of the distal tube. It is also understood that any embodiment of the support membrane as disclosed or contemplated herein can also be incorporated into any other known catheter. FIG. 18 depicts one embodiment of a catheter 400 in which the distal tube 404 has a support membrane 406 disposed around and coupled to the external wall 408 of the distal tube 404. More specifically, in this exemplary embodiment, the membrane 406 is disposed around a portion of the wall 408 and extends longitudinally along the length of the tube 404 such that the proximal end of the membrane 406 does not extend to the proximal end 410 of the tube 404. That is, the membrane 406 is positioned such that it is spaced from the proximal end 410 of the tube 404. Alternatively, the membrane 406 can extend to the proximal end 410 of the tube 404. According to certain implementations, the membrane 406 is disposed in the connection zone (or region) of the distal tube 404 in which the manipulation shaft 402 is coupled to the tube 402 (similar to the connection zone 42 discussed above with respect to FIG. 3A).

Figure 19:
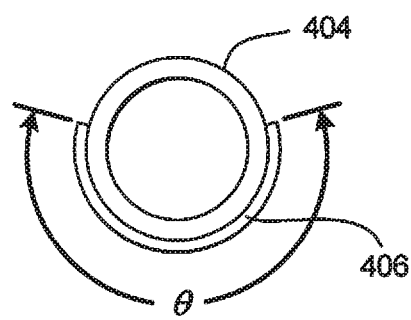
FIG. 19 is a cross-sectional view of a distal tube of a catheter with a support membrane, according to one embodiment.

The membrane 406 (and any other membrane embodiment disclosed or contemplated herein) can wrap or otherwise be disposed around a portion of the circumference of the tube 404 as shown. Alternatively, the membrane can be an additional tube or tube layer that is disposed around the entire circumference of the tube 404. In a further alternative, the membrane can be disposed around ¼, ½, or ¾ of the circumference of the tube 404. In yet another alternative, as best shown in FIG. 19, the membrane 406 can be disposed around any amount of the circumference of the tube 404. That is, the membrane 406 can cover any amount of the circumference of the tube 404 from about 30 degrees to about 360 degrees of the circumference. It is understood that these characteristics can apply to any membrane embodiment disclosed or contemplated herein that is disposed around any tube, including any catheter tube.

The membrane 406 (and any other membrane embodiment disclosed or contemplated herein) can have any size, shape, or configuration. In certain implementations, the membrane can be circular, oval, or an ellipse. Further, any of the membrane embodiments disclosed or contemplated herein is not necessarily a unitary, uniform component. Instead, any membrane embodiment can have one or more openings defined therein. In certain implementations, the one or more openings can be one or more channels defined in the membrane. Alternatively, membrane can have any pattern, feature, or configuration that forms any shape or shapes.

The various membrane embodiments disclosed herein (including membrane 406) can be made of any polymeric or non-polymeric material or any other known material that can be positioned around a catheter tube and is high strength and/or puncture resistant. For example, in one embodiment in which the material is polymeric, the material can be PTFE (etched or non-etched), PET, or PEEK or any other known polymeric material with the appropriate high strength and/or puncture resistance characteristics. In one embodiment, the membrane (such as membrane 406) has a thickness ranging from about 0.00025 inches to about 0.2 inches. Alternatively, the membrane can have a thickness ranging from about 0.001 inches to about 0.005 inches.

The membrane 406 (or any other membrane implementation disclosed or contemplated herein) can be attached to the external wall (such as wall 408) of the tube (such as tube 404) in a reflow process (in which the tube materials are heated/melted and the membrane is heat bonded to the tube), via adhesive bonding, or any other known method of attachment.

Figure 20:
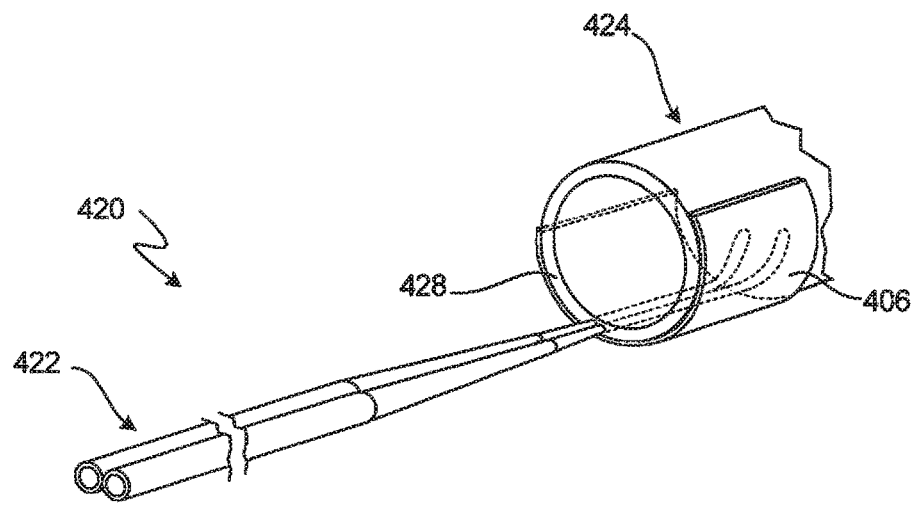
FIG. 20 is a perspective view of a portion of another catheter with a support membrane, according to another embodiment.

FIG. 20 shows another embodiment of a catheter 420 with a membrane 426 disposed around the connection zone of the manipulation shaft 422 and the distal tube 424. In this embodiment, the membrane 426 covers more of the circumference of the tube 424 in comparison to the membrane 406 discussed above and depicted in FIG. 19. Further, in this implementation, the membrane extends longitudinally along the length of the tube 424 such that the proximal end of the membrane 426 extends to the proximal end 428 of the tube 424. That is, the proximal end of the membrane 426 is positioned at the proximal end 428 of the tube 424. Alternatively, the membrane 426 can be spaced from the proximal end 428 of the tube 424.

Figure 21:
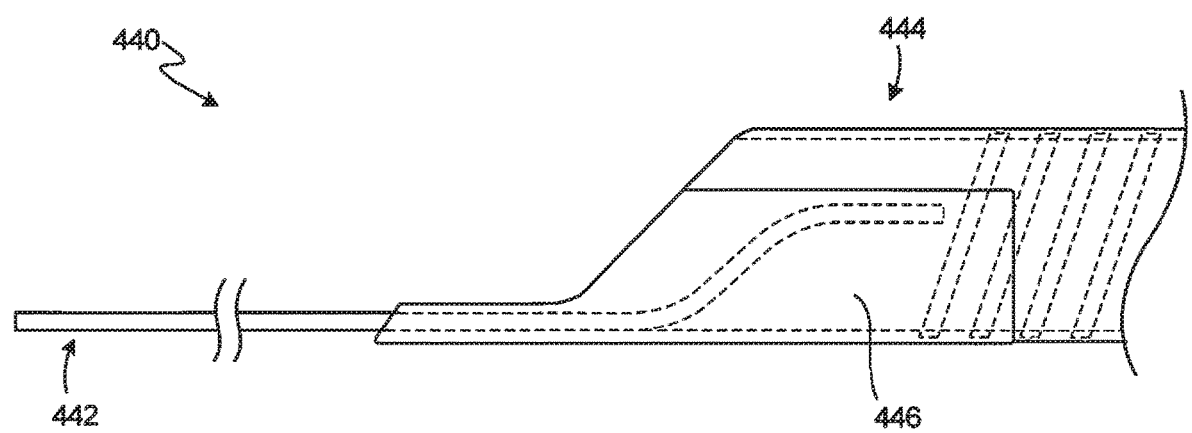
FIG. 21 is a side view of a portion of another catheter with a support membrane, according to a further embodiment.

A side view of another embodiment is shown in FIG. 21 in which the membrane 446 is positioned around the connection zone of the manipulation shaft 442 and the distal tube 444 of the catheter 440.

Figure 22:
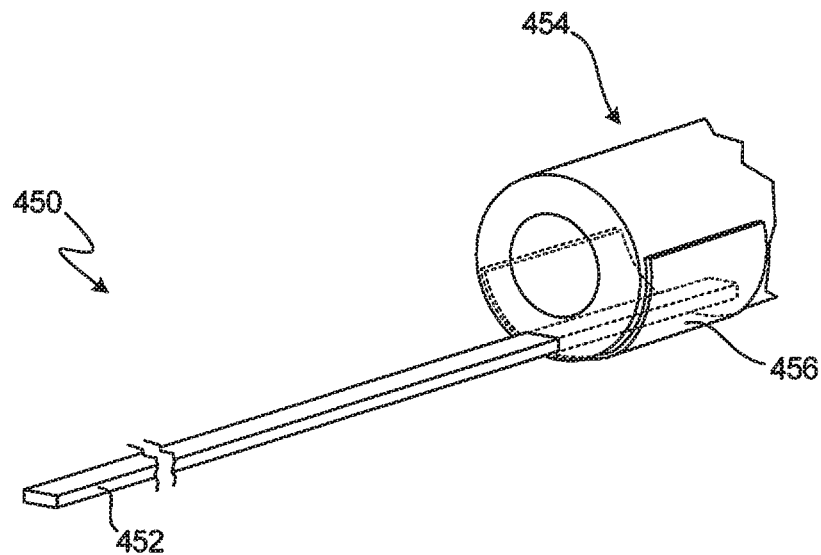
FIG. 22 is a perspective view of a portion of another catheter with a support membrane, according to yet another embodiment.

As mentioned above, any embodiment of the support membrane can also be incorporated into any other known catheter. For example, in another implementation as depicted in FIG. 22, the membrane 456 is positioned around the connection zone of the manipulation shaft 452 and the distal tube 454 of the catheter 450. In this embodiment, the manipulation shaft 452 is a flat or substantially square shaft or wire 452. Alternatively, the shaft 452 can have any known cross-sectional shape for a known component of a catheter. In further implementations, the shaft 452 can be tapered along some portion of its length or the entire length thereof.

Figure 23:
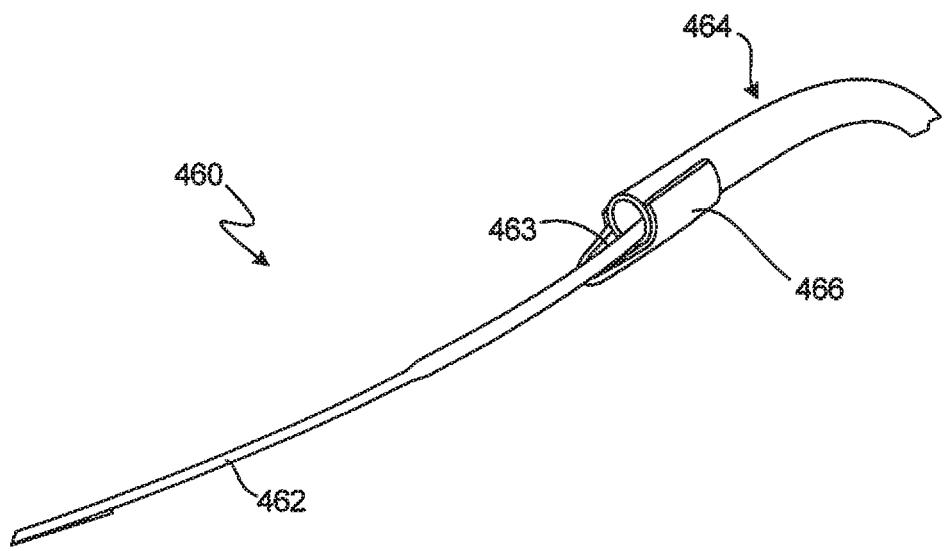
FIG. 23 is a perspective view of a portion of another catheter with a support membrane, according to a further embodiment.

In a further embodiment as shown in FIG. 23, the membrane 466 can be positioned around another known catheter. In this implementation, the catheter 460 has a manipulation shaft 462 that can be a solid wire or hollow tube that is further joined to a cylindrical or partially-cylindrical structure 463. The structure 463 is embedded within, or joined to, the wall at the proximal end of the distal tube 464. In certain embodiments, the structure 463 can be slotted or have a pattern formed therein to enhance attachment and flexibility. The support membrane 466 is positioned around the circumference or a portion of the circumference of the distal tube 464 in the connection zone extending distally on the distal tube from the structure 463. In certain embodiments, the support membrane 466 can enhance or strengthen the attachment of the structure 463 and the distal tube 464.

Figure 24:
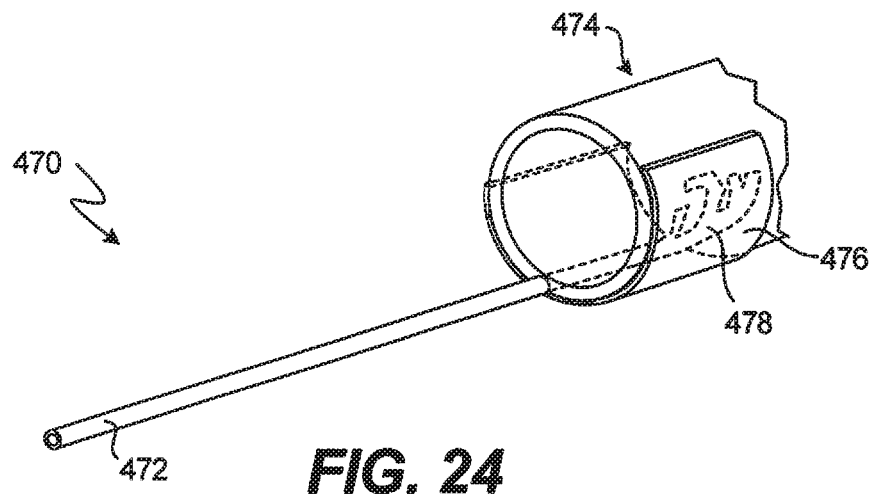
FIG. 24 is a perspective view of a portion of another catheter with a support membrane, according to another embodiment.

In yet another implementation as shown in FIG. 24, the membrane 476 can be positioned around another known catheter. That is, the membrane 476 is positioned around the connection zone of the manipulation shaft 472 and the distal tube 474 of the catheter 470. In this embodiment, the manipulation shaft 472 has an extension 478 that extends into and is embedded within the proximal end of the distal tube 474 as shown. The extension 478 in this embodiment has a configuration or features that strengthen the connection between the manipulation shaft 472 and the tube 474, thereby reducing the risk of separation of those two components.

Without being limited by theory, it is believed that the membrane embodiments disclosed herein provide a higher strength bond for the proximal portion of the distal tube that the membrane is disposed around, along with enhanced torque, peel, and shear strength. In those implementations in which the membrane disposed around the proximal portion is disposed around the connection zone of the catheter, the added strength bond can increase tensile strength and help prevent or reduce the risk of delamination, thereby preventing or reducing the risk of separation of the proximal manipulation shaft from the distal tube. That is, the membrane can provide fatigue resistance at the connection zone. In known fatigue testing of known catheters, application of repeated stress to the connection zone of the catheters caused the proximal shaft to separate from the distal tube (which could result in detachment proximal shaft from the distal tube or embolization during use). The membrane embodiments disclosed herein can reduce or prevent the risk of such separation. In addition, the membrane embodiments can also provide enhanced lubricity and additional strain relief properties.

In certain embodiments as discussed above, the membrane is disposed around a portion of the circumference of the tube, rather than the entire circumference. According to certain implementations, any membrane disposed around less than the entire circumference can be called a "partial circumference membrane." One advantage of a partial circumference membrane made of a high strength material such as those discussed above is that it provides support without fully encircling the tube. It is understood that a membrane made of a high strength material (such as PTFE or PEEK) that fully encircles the catheter tube could cause the catheter tube to malfunction or not function properly. That is, the high strength material positioned entirely around the tube could render that portion of the tube too inflexible or otherwise inoperable for its desired purpose. Thus, in those circumstances, a partial circumference membrane can utilize a high strength material while not rendering the catheter tube hindered or inoperable.

Further, a partial circumference membrane can also have the advantage of providing the thinnest thickness (or lowest profile) possible when adding an additional layer to a tube. That is, a membrane that encircles the entire circumference of a tube will add more outer diameter to the tube than a partial circumference membrane. As such, any partial circumference membrane can minimize the additional circumference of a tube when the membrane is added thereto.

Certain additional embodiments as disclosed and contemplated herein relate to an improved proximal portion of a catheter tube that can be incorporated into any known multi-layer catheter, including any catheter disclosed herein or any other catheter for use in a human patient. As will be explained in further detail below, the various improved proximal tube portion embodiments disclosed herein have a protective wrap disposed at the proximal portion of the tube that eliminates any exposed ends of the tubular layers. It is understood that the improved proximal tube portion embodiments are substantially similar to the improved catheter tip embodiments discussed above.

Figure 25:
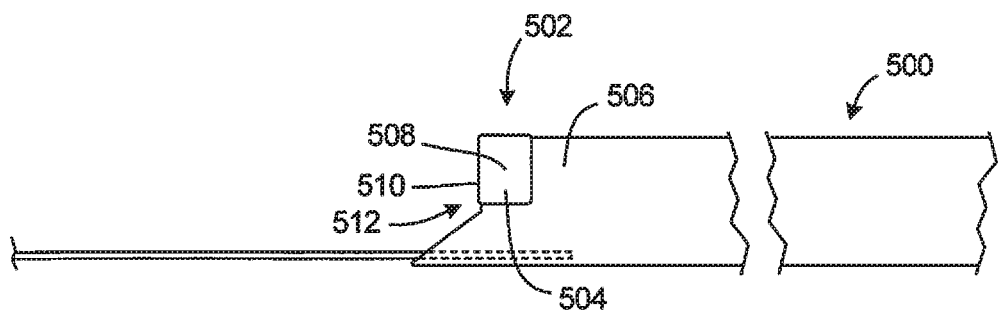
FIG. 25 is a side view of a portion of a catheter with a proximal protective wrap, according to one embodiment.

One embodiment of catheter tube 500 with an improved proximal portion 502 is depicted in FIG. 25. The tube 500 has a first layer (which, in this example, is also an inner layer) 504 and a second layer (which, in this example, is also an outer layer) 506. The two layers 504, 506 are positioned adjacent to each other and are adhered, coupled, or otherwise attached to each other along a substantial length of each. At least a portion of the inner layer 504 is a protective wrap (also referred to as an "extended portion," "extension," "distal wrap," or "protective tip") 508 that extends beyond the length of the outer layer 506 and, in this implementation, is wrapped around at least a portion of the distal end of the outer layer 506 as shown such that the external portion (also referred to as "outer portion" or "distal portion") of the extended portion 508 extends toward the distal end of the tube 500 and is positioned against or adjacent to the exterior surface of the outer layer 506. This configuration creates a fold 510 (also referred to herein as a "distal fold") of the extended portion 508 along at least a portion of the proximal end 512 of the tube 500 that facilitates protection of the tube layers at the end 512. In other words, the positioning of the extended portion 508 as shown ensures that the ends of the layers 504, 506 are not exposed along that portion of the proximal end 512 of the tube 500 covered by the wrap 508, thereby reducing the risk of delamination and the problems related thereto.

In this particular embodiment, the protective wrap 508 is integral with and is an extended portion of the inner layer 504. Alternatively, in any of the improved proximal tube portion embodiments disclosed or contemplated herein, the protective wrap (such as protective wrap 508) can be a separate component that is coupled to at least a portion of the distal ends of the inner layer (in this example, the inner layer 504) and the outer layer (in this case, the outer layer 506). In a further alternative, in any of the proximal tube portion embodiments disclosed or contemplated herein, the protective wrap (such as protective wrap 508) can be integral with and an extended portion of the outer layer (such as outer layer 506).

Figure 26:
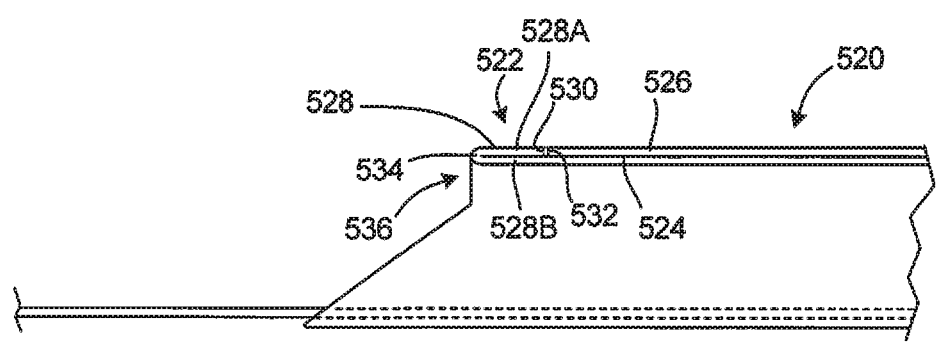
FIG. 26 is a side view of a portion of a catheter with a proximal protective wrap, according to another embodiment.

FIG. 26 shows another embodiment of a catheter tube 520 with an improved proximal tube portion 522. The tube 520 has a first (or "inner") layer 524 and a second (outer) layer 526 that are positioned adjacent to each other and are attached to each other along a substantial length thereof. In this implementation, the protective wrap 528 is an extended portion 528 of the inner layer 524 that extends beyond the length of the outer layer 526 and, in this implementation, is folded such that the external portion or outer portion (also referred to herein as the "distal portion") 528A of the extended portion 528 is positioned against or adjacent to the internal portion or inner portion (also referred to herein as the "proximal portion") 528B along at least a portion of the circumference of the end 536 and the distal end 530 of the external portion 528A is positioned against or attached to the proximal end 532 of the outer layer 526. This configuration creates a fold 534 (also referred to herein as a "distal fold") of the extended portion 528 at the proximal end 536 along at least a portion of the end 536 that facilitates protection of the tube layers at the end 536. Like the embodiment depicted in FIG. 25, the configuration of the protective wrap 528 as shown ensures that at least a portion of the ends of the layers 524, 526 are not exposed at the proximal end 536 of the tube 520, thereby reducing the risk of delamination and the problems related thereto.

Additional implementations similar to those discussed above with respect to FIGS. 15-17 and any other embodiments contemplated in the discussion above are also contemplated for the proximal tube end improvements. That is, any features or configurations of the improved distal tip embodiments discussed above and depicted in FIGS. 15-17 can also be incorporated into any of the embodiments of the improved proximal portions as discussed above and depicted in FIGS. 25-26. However, in certain embodiments of the improved proximal portion as noted above, the protective wrap does not extend around the entire circumference of the proximal end of the tube. As discussed above, it is also understood that the improved proximal end embodiments disclosed or contemplated herein can be incorporated into any known multi-layer catheter devices. Further, it is understood that any of the various improved proximal end embodiments disclosed or contemplated herein can be integrated into or combined with any boosting catheter, including the boosting catheter disclosed and claimed in U.S. application Ser. No. 14/210,572, entitled "Boosting Catheter and Related Systems and Methods," which is hereby incorporated herein by reference in its entirety.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

What is claimed is:

1. A catheter comprising:
   (a) a distal tube comprising a tubular wall and a tube lumen defined within the tube by the tubular wall; and
   (b) a proximal shaft operably coupled to a proximal portion of the distal tube, the proximal shaft comprising:
      (i) a first elongate member;
      (ii) a second elongate member; and
      (iii) at least two bindings formed between outer surfaces of the first and second elongate members, wherein the at least two bindings are spaced from each other and disposed along an entire length of the proximal shaft,
      wherein the first and second elongate members are configured to extend distally into a portion of the distal tube,
      wherein the first and second elongate members and the at least two bindings are configured to provide torque transmission to the distal tube via the proximal shaft.

2. The catheter of claim 1, further comprising a non-bound portion defined between each two of the at least two bindings.

3. The catheter of claim 1, wherein a total length of the at least two bindings is less than a total length of the first and second elongate members.

4. The catheter of claim 1, wherein the proximal shaft comprises a first sheath segment disposed around a first length of the first and second elongate members such that the first length of the first and second elongate members is disposed within the first sheath segment.

5. The catheter of claim 4, wherein the proximal shaft comprises at least one additional sheath segment, wherein each of the at least one additional sheath segments is disposed around a different length of the first and second elongate members.

6. The catheter of claim 5, wherein the proximal shaft comprises at least one unsheathed segment wherein a length of the first and second elongate members is not disposed within the sheath.

7. The catheter of claim 4, further comprising a filler material disposed within at least a portion of the first sheath segment.

8. The catheter of claim 4, wherein the proximal shaft further comprises a shaft lumen defined by the first sheath segment.

9. The catheter of claim 1, wherein the first elongate member is configured to extend distally into a first portion of the tubular wall, and further wherein the second elongate member is configured to extend distally into a second portion of the tubular wall.

10. The catheter of claim 1, further comprising at least one support member disposed in the proximal portion of the distal tube.

11. The catheter of claim 1, wherein the proximal shaft comprises at least one additional elongate member.

12. The catheter of claim 1, wherein characteristics of the at least two bindings influence torsional compliance characteristics of the proximal shaft.

13. The catheter of claim 1, wherein the first and second elongate members are moveable in relation to each other along each non-bound portion.

14. The catheter of claim 1, wherein the first and second elongate members are disposed in rolling contact with each other.

15. The catheter of claim 1, wherein an increase in length or number of the at least two bindings decreases the torsional compliance characteristics of the proximal shaft.

16. The catheter of claim 1, wherein a decrease in length or number of the at least two bindings increases the torsional compliance characteristics of the catheter.

17. A catheter comprising:
   (a) a distal tube comprising a tubular wall and a tube lumen defined within the tube by the tubular wall;
   (b) a support membrane disposed around a portion of the distal tube; and
   (c) a proximal shaft operably coupled to a proximal portion of the distal tube, the proximal shaft comprising:
      (i) a first elongate member, wherein the first elongate member is a solid rod;
      (ii) a second elongate member, wherein the second elongate member is a solid rod; and
   (iii) at least two bindings formed between outer surfaces of the first and second elongate members, wherein the at least two bindings are spaced from each other and disposed along an entire length of the proximal shaft,
      wherein the first and second elongate members are configured to extend distally into a portion of the distal tube,
      wherein the first and second elongate members and the at least two bindings are configured to provide torque transmission to the distal tube via the proximal shaft.

18. The catheter of claim 17, wherein the support membrane is a partial circumference membrane.

19. The catheter of claim 17, wherein the distal tube further comprises a protective wrap disposed around a portion of a proximal opening of the distal tube.

20. The catheter of claim 17, wherein the distal tube comprises a distal portion that has a higher stiffness than a proximal portion.

21. The catheter of claim 17, further comprising a non-bound portion defined between each two of the at least two bindings.

22. The catheter of claim 17, wherein the proximal shaft comprises a first sheath segment disposed around a first length of the first and second elongate members such that the first length of the first and second elongate members is disposed within the first sheath segment.

23. The catheter of claim 22, wherein the proximal shaft comprises at least one additional sheath segment, wherein each of the at least one additional sheath segments is disposed around a different length of the first and second elongate members.

24. The catheter of claim 23, wherein the proximal shaft comprises at least one unsheathed segment wherein a length of the first and second elongate members is not disposed within the sheath.

25. The catheter of claim 17, wherein characteristics of the at least two bindings influence torsional compliance characteristics of the proximal shaft.

26. The catheter of claim 17, wherein the first and second elongate members are moveable in relation to each other along each non-bound portion.

27. The catheter of claim 17, wherein the first and second elongate members are disposed in rolling contact with each other.

28. The catheter of claim 17, wherein an increase in length or number of the at least two bindings decreases the torsional compliance characteristics of the proximal shaft.

29. The catheter of claim 17, wherein a decrease in length or number of the at least two bindings increases the torsional compliance characteristics of the catheter.

30. A method of using an extension catheter in combination with a standard guiding catheter to perform a procedure at a predetermined location within the vasculature of a patient, the method comprising:

positioning the standard guiding catheter into a target vessel in the patient;

selecting the extension catheter based on desired torsional compliance characteristics, the extension catheter comprising:

(a) a distal tube comprising a tubular wall and a tube lumen defined within the tube by the tubular wall;

(b) a proximal shaft operably coupled to a proximal portion of the distal tube, the proximal shaft comprising:

(i) a first elongate member;
      (ii) a second elongate member; and
      (iii) at least two bindings formed between outer surfaces of the first and second elongate members, wherein the at least two bindings are spaced from each other and disposed along an entire length of the proximal shaft, wherein the torsional compliance characteristics are determined based at least in part on the at least two bindings;

inserting the extension catheter into the standard guiding catheter;

urging the extension catheter distally through the standard guiding catheter by urging the proximal shaft distally such that torque transmission created by the first and second elongate members and the at least two bindings causes the distal tube to rotate and move distally such that a distal portion of the distal tube extends distally out of the distal end of the standard guiding catheter; and performing a procedure through the extension catheter and standard guiding catheter.

31. The method of claim 30, wherein characteristics of the at least two bindings influence torsional compliance characteristics of the proximal shaft.

32. The method of claim 30, wherein the first and second elongate members are moveable in relation to each other along each non-bound portion.

33. The method of claim 30, wherein an increase in length or number of the at least two bindings decreases the torsional compliance characteristics of the proximal shaft.

34. The method of claim 30, wherein a decrease in length or number of the at least two bindings increases the torsional compliance characteristics of the proximal shaft.

* * * * *